(12) United States Patent
Holderby

(10) Patent No.: US 11,147,664 B2
(45) Date of Patent: Oct. 19, 2021

(54) INTRAOCULAR LENS INJECTOR

(71) Applicant: Alcon Inc., Fribourg (CH)

(72) Inventor: Victoria Holderby, Arlington, TX (US)

(73) Assignee: Alcon Inc., Fribourg (CH)

( * ) Notice: Subject to any disclaimer, the term of this patent is extended or adjusted under 35 U.S.C. 154(b) by 204 days.

(21) Appl. No.: 16/507,418

(22) Filed: Jul. 10, 2019

(65) Prior Publication Data

US 2020/0015960 A1   Jan. 16, 2020

Related U.S. Application Data

(60) Provisional application No. 62/696,090, filed on Jul. 10, 2018.

(51) Int. Cl.
*A61F 2/16*   (2006.01)
*A61F 9/00*   (2006.01)
*A61F 9/007*  (2006.01)

(52) U.S. Cl.
CPC ............ *A61F 2/167* (2013.01); *A61F 2/1691* (2013.01); *A61F 9/0017* (2013.01); *A61F 9/00736* (2013.01)

(58) Field of Classification Search
CPC ...... A61F 2/167; A61F 2/1691; A61F 9/0017; A61F 9/00736; A61M 5/31526; A61M 5/31581; A61M 2005/31506; A61M 2005/31508; A61M 2005/3151; A61M 2005/31516; A61M 2005/31518; A61M 2005/3152; A61M 2005/31521; A61M 2005/31523; A61M 2005/31588; A61M 5/315; A61M 5/31501; A61M 5/31505; A61M 5/31511; A61M 5/31513; A61M 5/31515; A61M 5/31576; A61M 5/31578; A61M 5/3158; A61M 5/31583; A61M 5/31585; A61M 5/31586; F16H 33/00; F16H 33/02; F16H 33/04

See application file for complete search history.

(56) References Cited

U.S. PATENT DOCUMENTS

| | | | |
|---|---|---|---|
| 7,156,854 B2 | 1/2007 | Brown et al. | |
| 2013/0060257 A1* | 3/2013 | Meyer | A61F 2/167 606/107 |
| 2015/0209821 A1* | 7/2015 | Pfahnl | A61M 5/3148 222/1 |
| 2016/0256316 A1 | 9/2016 | Van Noy et al. | |
| 2017/0172727 A1 | 6/2017 | Kanner et al. | |
| 2017/0245984 A1* | 8/2017 | Germann | A61M 5/31581 |
| 2017/0296753 A1 | 10/2017 | Rowe et al. | |

FOREIGN PATENT DOCUMENTS

| | | | |
|---|---|---|---|
| EP | 0363213 A2 | 4/1990 | |
| GB | 2405344 A * | 3/2005 | .......... A61F 2/1664 |
| GB | 2405344 A | 3/2005 | |

* cited by examiner

*Primary Examiner* — Erich G Herbermann
*Assistant Examiner* — Chima U Igboko

(57) ABSTRACT

Intraocular lens (IOL) injectors are describe that include a rack and pinion to advance an IOL through the IOL injector and eject the IOL therefrom. IOL injectors described herein may also include a slide advance operable to advance an IOL from a storage location to a dwell location within the IOL injector.

18 Claims, 18 Drawing Sheets

INTRAOCULAR LENS INJECTOR

CROSS-REFERENCE TO RELATED APPLICATIONS

This application claims the benefit of U.S. Provisional Application No. 62/696,090, filed Jul. 10, 2018, the entire contents of which are incorporated herein by reference.

TECHNICAL FIELD

The present disclosure relates to ophthalmic surgery, and more specifically, to intraocular lens (IOL) injectors and related methods.

BACKGROUND

In ophthalmology, eye surgery, or ophthalmic surgery, saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Light enters the human eye through a clear cornea that is located on the outer part of the eye and covers the pupil and iris. The light travels through the pupil and then encounters the lens, located behind the iris. As the light travels through the lens, the lens refracts the light so that it focuses on the retina, located in the back of the eye. Special cells in the retina detect the light and transmit signals based on the light via the optic nerve to the brain, which interprets the signals as vision.

Vision quality is, therefore, influenced by a number of factors, including the transparency and refractive properties of the cornea and the lens. Unfortunately, as people age or due to trauma or disease, the lens may be become less transparent and a cataract develops. Cataracts cause deterioration of vision and are often surgically corrected. During some cataract surgeries, the lens is surgically removed and replaced with an artificial intraocular lens (IOL).

Many cataractous lenses are removed by a surgical technique called phacoemulsification. During this procedure, an opening is made in the anterior capsule and a phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens, also referred to as an intraocular lens (IOL).

The IOL is injected into the eye through a small incision, sometimes the same incision used to remove the diseased lens. An IOL injector is used to deliver an IOL into the eye.

SUMMARY

According to a first aspect, the present disclosure relates to an intraocular lens (IOL) injector. The IOL injector may include an injector body and a plunger at least partially disposed in the injector body and moveable therein. The injector body may include a main body a nozzle coupled to a distal end of the main body. The IOL injector may include a bore that extends through the nozzle; a pinion pivotably coupled to the injector body and comprising a plurality of teeth; and a rack disposed on the plunger body and comprising a plurality of teeth. The pinion and the rack may be interoperable to advance the plunger in a first axial direction towards a distal end of the nozzle in response to a rotation of the pinion. The plunger may include a plunger rod coupled to a distal end of the plunger body and a plunger tip formed at a distal end of the plunger rod, the plunger tip adapted to contact an IOL. The plunger may be movable a first distance within the injector body in response to an axial force applied to the plunger free from engagement between the rack and the pinion, and the plunger may be moveable in response to rotation of the pinion over a second distance within the injector body when the pinion is rotatably coupled with the rack and the plunger.

The main body may include a slot. The plunger may include a flange extending through the slot. The flange may be displaceable in the slot to move the plunger from a first position to a second position. Movement of the flange from the first position to the second position may be operable to displace an IOL from a storage position in the nozzle to a dwell position in the nozzle. The flange may be detachable from the plunger. Movement of the plunger from the first position to the second position may move the plurality of teeth of the pinion and the plurality of teeth of the rack from an unmeshed relationship into an intermeshing relationship. A barrier may be adapted to engage the flange to define the second position. The plunger may include a flange disposed at a proximal end of the plunger body. The main body may include a barrier formed therein and a proximal opening. The flange may be moveable into the proximal opening of the main body and engageable with the barrier to define the second position when the plunger is distally displaced within the injector body. The first plurality of teeth of the pinion may be adapted to intermesh with the plurality of teeth of the rack such that rotation of the pinion in a first rotational direction displaces the plunger in the first axial direction. The pinion may be a first pinion. A second pinion may be interposed between the first pinion and the rack. The rotation of the first pinion in a first rotational direction may displace the plunger in the first axial direction. The second pinion may include a plurality of teeth that intermeshes with both the plurality of teeth of the first pinion and the plurality of teeth of the rack. A ratio of a diameter of the first pinion to a diameter of the second pinion may be in a range of 1:1 to 5:1. The ratio may be 3:1. A wheel may be coupled to the pinion and accessible to a user. The pinion may be rotatable in response to a rotation of the wheel. A ratchet and pawl may be adapted to permit rotation of the pinion in a first rotational direction and prevent rotation of the pinon in a second rotational direction opposite the first rotational direction. A ribbed damper may include at least one rib on the plunger body and at least one rib on an interior wall of the main body. The at least one rib on the plunger may be adapted to contact the at least one rib on the interior wall and to provide frictional resistance to movement of the plunger in the first axial direction. One or more of the ribs on the plunger body may form a ridge, and one or more ribs on the interior wall may form a ridge-engaging tooth. The ridge and the ridge-engaging tooth may be adapted to prevent movement of the plunger in a second axial direction opposite the first axial direction. One or more of the ribs on the interior wall may forms a ridge, and one or more ribs on the plunger may form a ridge-engaging tooth. The ridge and the ridge-engaging tooth may be adapted to prevent movement of the plunger toward the proximal end of the main body of the IOL injector. The IOL injector may be adapted to separately inject an IOL base, an IOL optic, or both. The IOL injector may be adapted to concurrently inject an IOL base and an IOL optic.

BRIEF DESCRIPTION OF THE DRAWINGS

For a more complete understanding of the present disclosure and the associated features and advantages, reference is now made to the following description, taken in conjunction with the accompanying drawings, which are not to scale, and in which:

FIG. 10E is a cross-sectional view of another exemplary IOL injector having a slide advance and rack and pinion;

DETAILED DESCRIPTION

Figure 1:
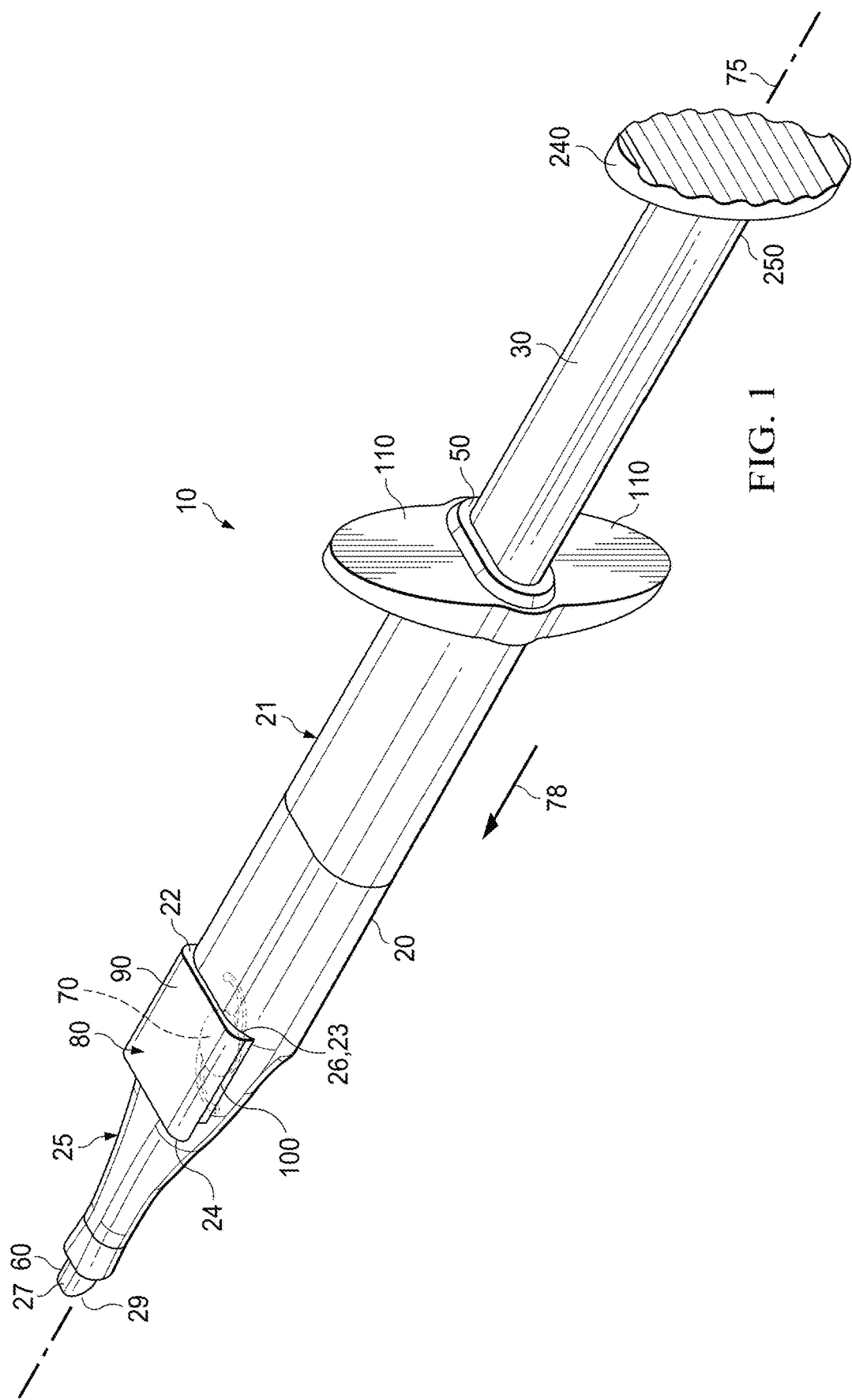
FIG. 1 is a perspective view of an example IOL injector.

In the following description, details are set forth by way of example to facilitate discussion of the disclosed subject matter. It should be apparent to a person of ordinary skill in the art, however, that the disclosed implementations are exemplary and not exhaustive of all possible implementations.

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

The present disclosure relates to ophthalmic surgery and, more specifically, to an intraocular lens (IOL) injector.

Following removal of a cataractous lens by phacoemulsification, the cataractous lens is replaced by an artificial lens, referred to herein as an IOL. The IOL is typically injected into the eye through the same small incision used to remove the diseased lens. IOL injector is used to deliver an IOL into the eye.

Figure 2:
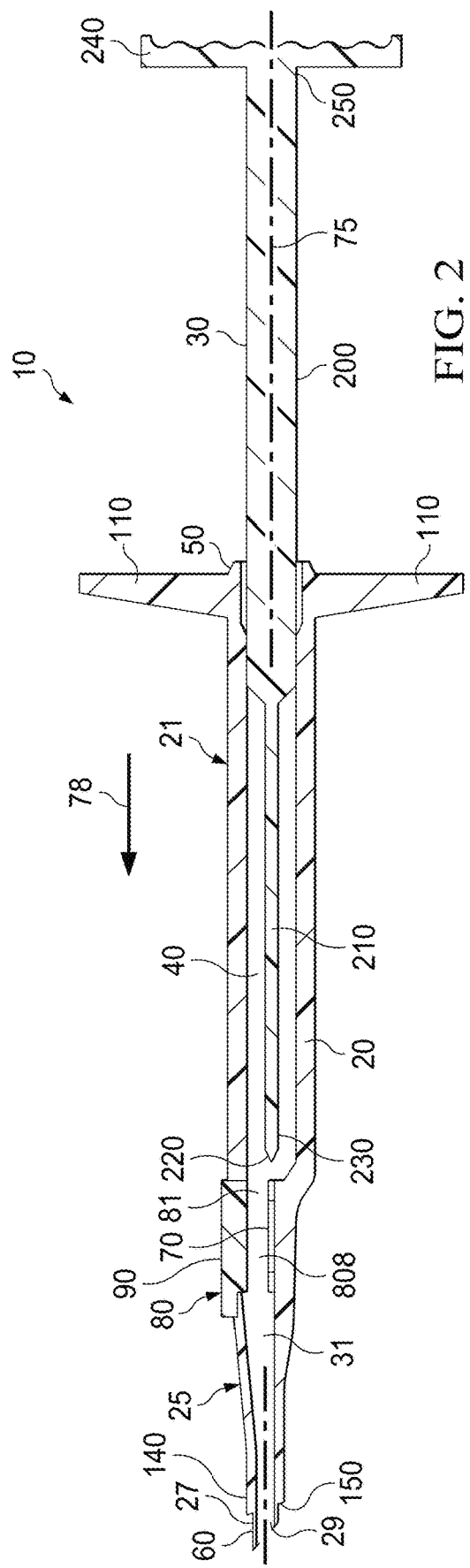
FIG. 2 is a longitudinal cross-sectional view of the exemplary IOL injector of FIG. 1.

FIGS. 1 and 2 are schematics of an exemplary IOL injector 10. The IOL injector 10 has an injector body 20. The injector body 20 includes a main body 21 having a proximal end 50 and a distal end 22. The injector body 20 includes an injector nozzle 25 having a proximal end 23 and a distal end 60. The nozzle 25 defines a passage 31. The proximal end 23 of the injector nozzle 25 is coupled to the distal end 22 of the main body 21. A proximal portion of the nozzle 25 includes an IOL storage compartment 80 that defines a cavity 81 operable to house an IOL 70 prior to insertion into an eye. The nozzle 25 also includes a distal tip 27 that defines an opening 29 through which the IOL is delivered out of the IOL injector 10. In some implementations described herein, the storage compartment 80 defines an IOL storage location 808. The IOL storage compartment 80 has a proximal end 26 and a distal end 24, the proximal end 26 of the IOL storage compartment 80 being coupled to the distal end 22 of the main body 21. In some instances, a door 90 may be included to provide access to the IOL storage compartment 80. The door 90 may include a hinge 100 such that the door 90 may be pivoted about the hinge 100 to open the IOL storage compartment 80. The injector body 20 defines a bore 40 that joins and is fluid communication with the opening 29. A longitudinal axis 75 extends along the bore 40. The injector body 20 may also include tabs 110, for example formed at the proximal end 50 of the main body 21. Other configurations are possible. For example, in other implementations, the tabs 110 may be located at the distal end 22 of the main body 21. The tabs 110 may be manipulated by fingers of a user, such as an ophthalmologist or other medical professional, to advance the plunger 30 (discussed below) through the bore 40.

In some implementations, various manipulations of the IOL injector 10, and various method steps, may be performed by one person, or by a plurality of persons. For example, some steps of methods described herein may be performed by a nurse, while other steps may be performed by an ophthalmic surgeon. For example, advancing an IOL 70 within the injector body 20 of an IOL injector 10 from a storage location 808 to a dwell location 809 (as shown, for example, in FIG. 9) may be performed by a nurse, while injection of the IOL 70 into an eye may be performed by a surgeon.

The IOL injector 10 also includes a plunger 30 received within the bore 40 and moveable therein such that the plunger 30 is slideable within the bore 40. As the plunger 30 is displaced distally within bore 40, the plunger 30 engages and advances an IOL, such as IOL 70, contained in the compartment 80.

As shown in FIG. 2, the plunger 30 includes a plunger body 200, a plunger rod 210 extending distally from the plunger body 200, and a plunger tip 220 formed at a distal end 230 of the plunger rod 210 and adapted to contact an IOL disposed, for example, within the IOL storage compartment 80 of the IOL injector 10. The plunger 30 may also include a flange 240 formed at a proximal end 250 of the plunger body 200. The plunger 30 is movable along the bore 40 in response to an axial force applied to the plunger 30 in the direction of arrow 78. The axial force may be applied to the flange 240, such as by a thumb of a user.

In some implementations described herein, various parts of the plunger 30 may be physically separated or decoupled from each other within the injector body 20 of the IOL injector 10. For example, in some implementations, the plunger body 200 may be physically separated or decoupled from the plunger rod 210. In various implementations, where various parts of the plunger 30 are physically separated or decoupled from each other, additional components of the IOL injector 10 may actuate movement of one part of the plunger 30 in response to movement of another part of the plunger 30.

Figure 3:
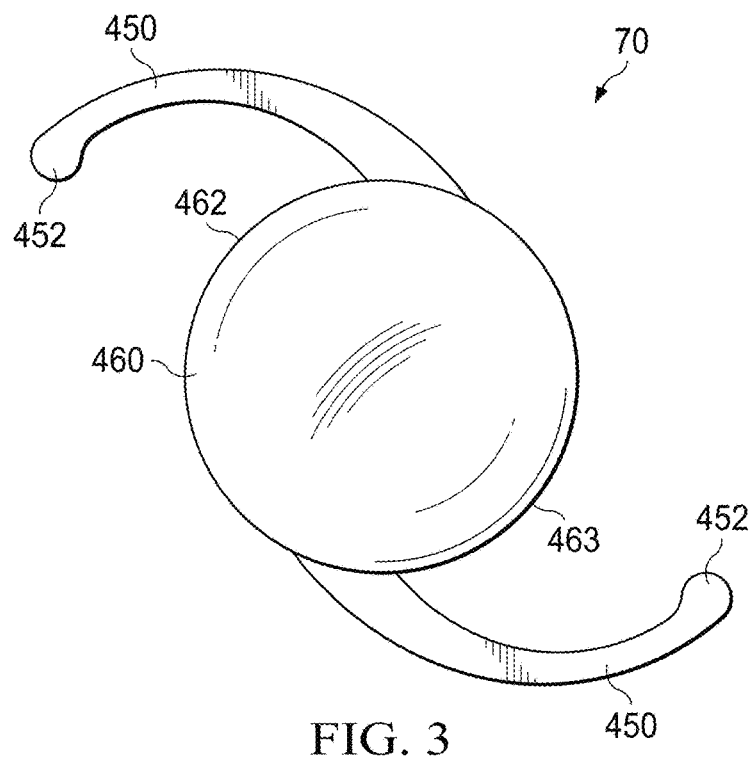
FIG. 3 shows an exemplary one-piece IOL.

In some implementations, the IOL 70 may be a one-piece IOL. That is, in some implementations, the IOL 70 may include an optic 460 and haptics 450, as shown in FIG. 3. Each of the haptics 450 includes a tip 452. In some implementations, the optic 460 and the haptics 450 may be integrally formed out of a single piece of material. In other implementations, the optic 460 may be formed out of one piece of material; the haptics 450 may be formed out of another piece of material; and the optic 460 and the haptics 450 may be coupled together prior to delivery into an eye. In some instances, the optic 460 and haptics 450 may be fixedly secured to each other prior to insertion into an IOL injector and delivered into an eye. The optic 460 includes a distal edge 462 and a proximal edge 463.

Figure 4:
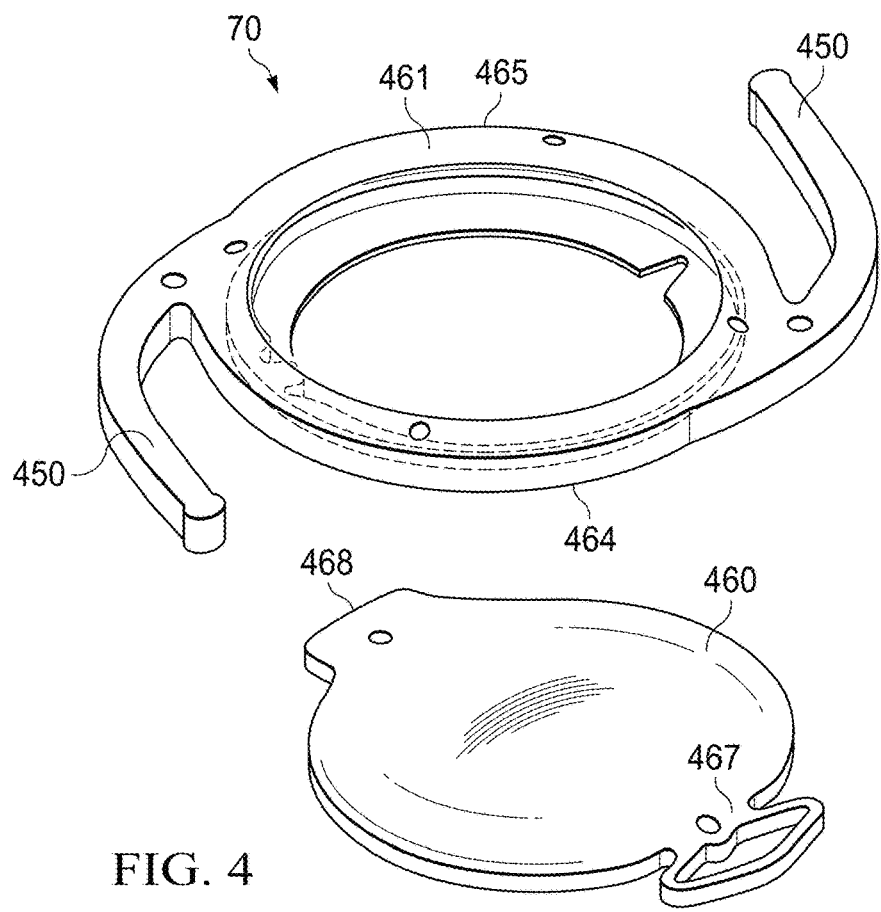
FIG. 4 shows an exemplary two-piece IOL including a base and an optic.

In other implementations, the IOL 70 may be a multi-piece IOL. For example, in some implementations, the IOL 70 be include two or more separate components. FIG. 4 is an example IOL 70 that includes two removably attached components. As shown in FIG. 4, the IOL 70 includes an optic 460 and a base 461 that includes haptics 450. The optic 460 and the base 461 are adapted to be coupled together into a unitary IOL and, thereafter, detached from each other into separate components, if desired. In some instances, one or more components of a multi-piece IOL, such as, for example the two-piece IOL 70 shown in FIG. 4, are separately injectable into a patient's eye. Once in the eye, the components may be assembled into a complete IOL. For example, for the two-piece IOL 70 shown in FIG. 4, the optic 460 and the base 461 are separately injectable into an eye. Once injected, the optic 460 is adapted to be coupled to and to rest on the base 461. The base 461 includes a distal edge 464 and a proximal edge 465. The optic 460 includes a distal edge 467 and a proximal edge 468.

Occasionally, patients may require replacement of an IOL, and a procedure to replace an IOL may result in damage to the eye. With the use of a two-piece IOL, for example, a replacement procedure may involve replacement only of the optic, allowing the base to remain in place within the eye.

As explained above, in some implementations, the IOL 70 may be a two-piece IOL wherein the base 461 and the optic 460 are separately injected into the patient's eye. Accordingly, for two-piece IOLs, the base 461 and the optic 460 may be contained in separate IOL injectors 10 for insertion in the eye. In other implementations, the two components of a two-piece IOL may be inserted into an eye separately using a single IOL injector. For a single-piece IOL, the optic 460 and haptics 450 form a unitary IOL and are inserted into an eye simultaneously with the use of a single IOL injector.

Accordingly, in some implementations, a user may place a one-piece IOL into an IOL injector, for example, by loading an IOL into the IOL storage compartment of the IOL injector, such as the IOL storage compartment 80 of the IOL injector described above. As also explained, the storage compartment may be accessed via a door, such as the door 90. In some implementations, the IOL may be manually folded into a compressed or folded configuration prior to installation into the IOL injector.

In the case of a two-piece IOL, in some implementations, a user may load the base (which may be similar to base 461) into an IOL storage compartment of an IOL injector, for example, via a door. The optic (which may be similar to optic 460) of may be introduced into the IOL storage compartment of separate IOL injector, for example, via a door. In some instances, the IOL storage compartment may be accessed through the door similar to door 90. In some implementations, one or both of the base and the optic may be manually folded into a compressed or folded configuration prior to installation into an IOL injector.

In some implementations, the IOL may be pre-loaded into the storage compartment of an IOL injector, for example, during manufacturing or otherwise prior to distribution to an end user. Accordingly, for the one-piece IOL, the one-piece IOL may be pre-loaded into the storage compartment an IOL injector prior to receipt by the end user. For a two-piece IOL, the base may be pre-loaded into a storage compartment of one IOL injector, while the optic may be pre-loaded into the IOL storage compartment of another IOL injector. The term "pre-loaded" as used herein means that an IOL, either in a one-piece or multi-piece configuration (including, for example, a two-piece configuration) is loaded into the IOL injector not by a user, but, rather, the IOL is installed and already contained within the IOL injector when the IOL injector is received by the user. For example, the IOL may be installed during manufacturing and prior the IOL injector being shipped to an end-user. The IOL injector(s) may be packaged within sterile packaging when received by a user.

As would be understood by persons of ordinary skill in the art, an IOL that is pre-loaded into an IOL injector has advantages over manual installation and folding of an IOL into the IOL injector that is performed by a user. For example, manual installation and folding of an IOL may allow more opportunity for errors, which have the potential to cause unnecessary secondary manipulation or correction during an already complex procedure. Manual installation and folding of an IOL may also introduce the possibility of contamination of the IOL, such as by human error or poor sterile technique. Contamination of the IOL may compromise the sterile environment for the patient and risk infection or other harm to the patient.

Figure 5:
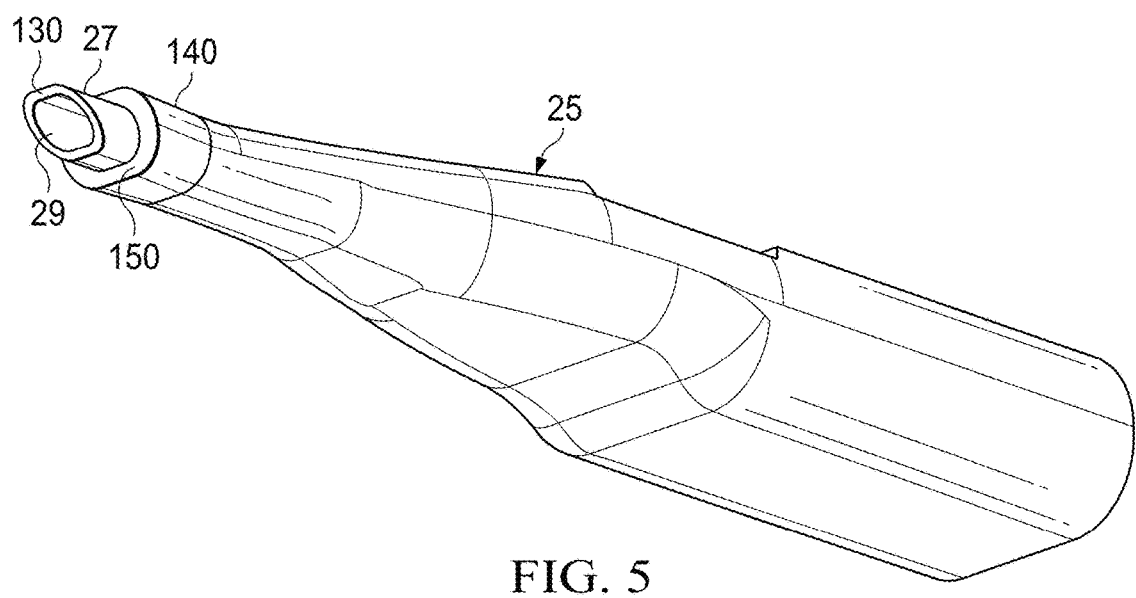
FIG. 5 is a perspective view of an exemplary nozzle of an IOL injector.
Figure 6:
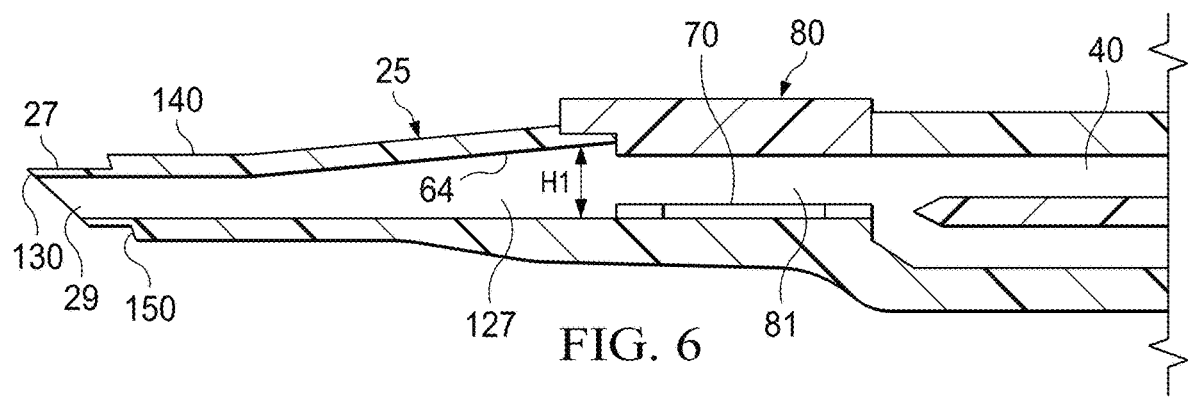
FIG. 6 is a cross-sectional view of the exemplary nozzle of an IOL injector shown in FIG. 5.
Figure 7:
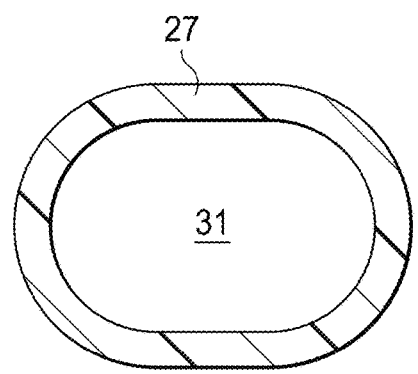
FIG. 7 is an exemplary cross-sectional view of a distal tip of a nozzle of an IOL injector.

FIGS. 5-7 illustrate details of the exemplary nozzle 25. In some instances, the nozzle 25 has a tapered exterior surface. Further, the passage 31 of the nozzle 25 may form part of the bore 40. The passage 31 tapers towards the opening 29. The distal tip 27 is adapted for insertion into an eye so that an IOL may be implanted. An IOL is expelled from the opening 29 formed in the distal tip 27. As shown in FIG. 7, the distal tip 27 may have an elliptical cross section. Additionally, the distal tip 27 may include a beveled tip 130. The cavity 81 of the storage compartment 80, passage 31, and opening 29 may define a delivery passage 127. A size of the delivery passage 127 may vary along a length thereof. That is, in some instances, a height H1 of the delivery passage 127 may change along a length thereof. The variation in size of the delivery passage 127 may contribute to the folding of the IOL as it is advanced therealong.

In some instances, the injector body 20 may include an insertion depth guard 140. The insertion depth guard 140 may form a flanged surface 150 that is adapted to abut an exterior eye surface. The insertion depth guard 140 abuts an eye surface and, thereby, limits an amount by which the distal tip 27 is permitted to extend into an eye, as described in U.S. application Ser. No. 15/049,315, the disclosure of which is being incorporated herein by reference in its entirety.

Figure 8:
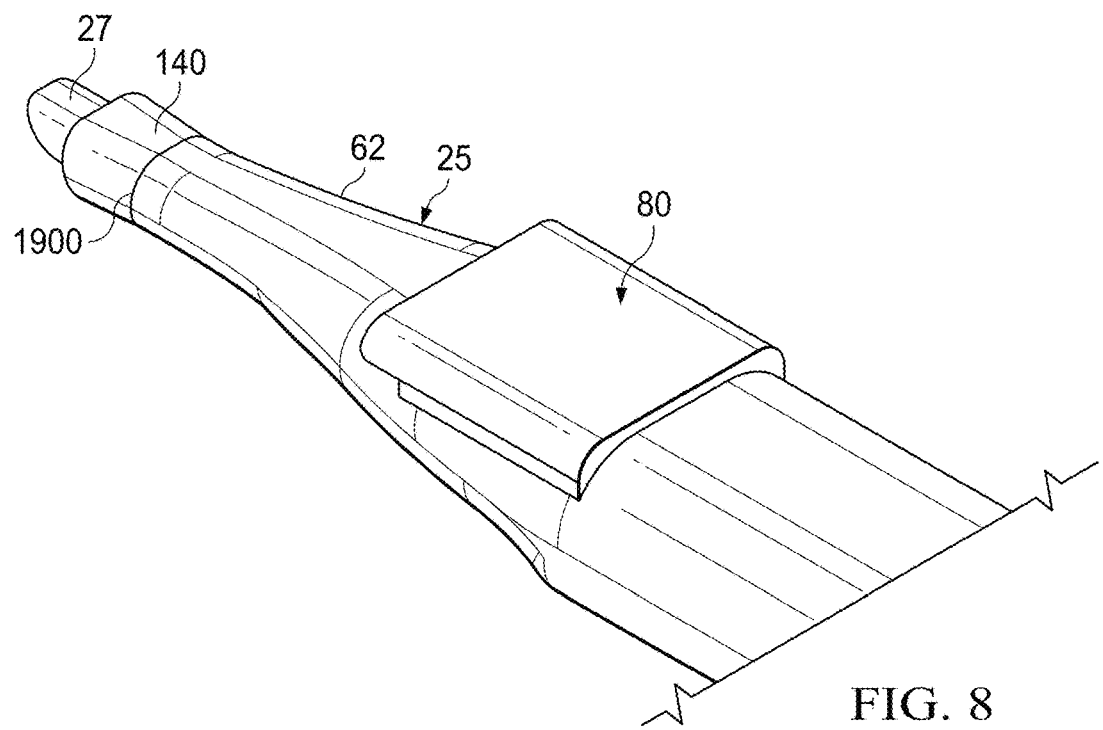
FIG. 8 is a detail view of an exemplary nozzle.

FIG. 8 is a detail view of a portion of the exemplary nozzle 25. The nozzle 25 may include a tapered portion 62 and the insertion depth guard 140. The distal tip 27 may include a demarcation 1900 that provides a visual indication of the dwell location 809 (shown, for example, in FIG. 9) of the folded or partially folded IOL 70. The term "dwell location" as used herein refers to a location adjacent to the distal end 60 of the nozzle 25 where an IOL would reside prior to being ejected from the IOL injector. For example, in some implementations, the dwell location 809 may be a location between 2 mm and 10 mm from the distal end 60. An IOL may be placed in dwell location prior to a surgical procedure. The IOL may be placed in the dwell location such as by a nurse or other medical professional that prepares the IOL injector for use. Placing an IOL in a dwell location provides for folding an IOL, either partially or fully, and for a decreased travel distance of the IOL when a physician takes possession of the IOL for implantation of the IOL into a patient's eye. Thus, placing an IOL placed at the dwell location may be a preparatory step performed by an assistant to a surgical procedure that allows the physician more quickly to perform the surgical procedure once the physician takes possession of the IOL injector. For example, in the example shown in FIG. 8, the demarcation 1900 is a narrow ridge or line that encircles all or a portion of the nozzle 25. In some instances, the demarcation 1900 may be formed into the nozzle 25, such by a recess or groove or a protruding ridge. In other implementations, the demarcation 1900 may be formed by a paint or other coating or an additive or insert applied to the material forming the nozzle 25, such as during manufacturing or sometime thereafter. In some instances, the demarcation 1900 may be disposed between the tapered portion 62 and the insertion depth guard 140. In implementations in which a depth guard 140 is omitted, the demarcation 1900 may located between the distal tip 27 and the tapered portion 62. At least a portion of the injector body 20 may be formed from a transparent or semi-transparent material that permits a user to see an IOL within the injector body 20. Particularly, the nozzle 25 of the injector body 20 may be formed from a transparent material to permit observation of the IOL as the IOL is moved therethrough by the plunger 30.

Figure 9:
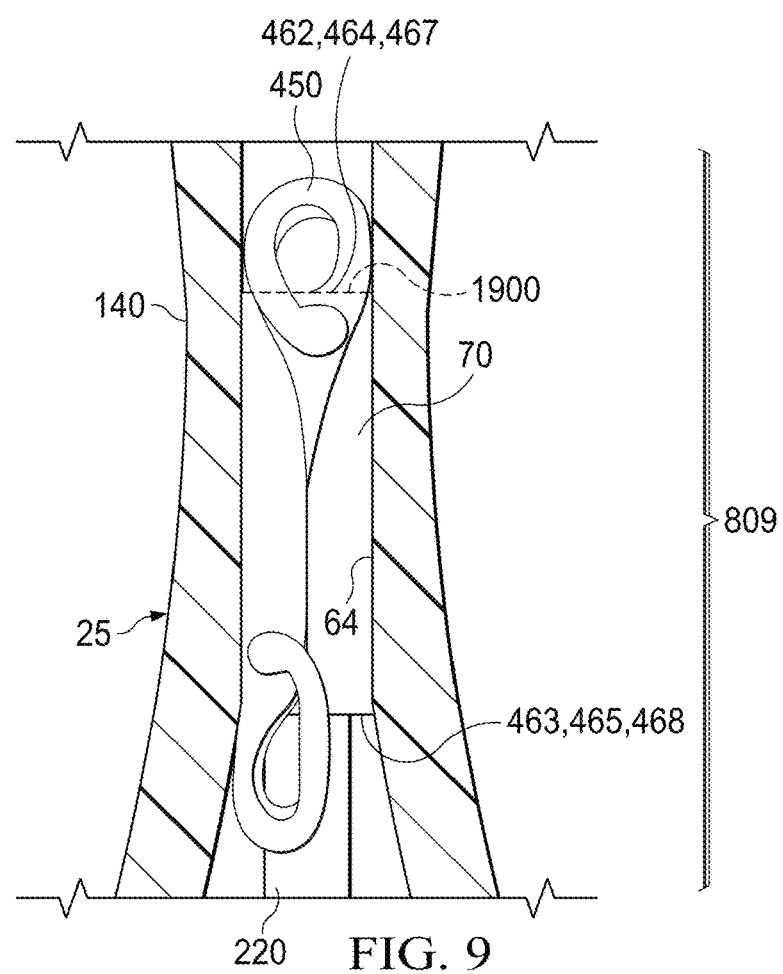
FIG. 9 is another detail view of a cross-section of an exemplary nozzle showing an IOL located at a dwell position.

FIG. 9 shows a view of the exemplary nozzle 25 with the IOL 70 located therein at the dwell location 809. A plunger 220 is shown contacting the proximal edge 463, 465, or 468. As shown in FIG. 9, the dwell location 809 of the IOL 70 may be defined as a location where a distal edge 462 of the optic 460 of the IOL 70 aligns with the demarcation 1900. In the case of a two-piece IOL, such as IOL 70 shown in FIG. 4, where the base 461 and optic 460 are implanted into an eye separately, the dwell location 809 of the two-piece IOL 70 may be defined as a location where a distal edge 467 of the optic 460 or the distal edge 464 of the base 461 aligns with the demarcation 1900. A haptic 450 or a portion thereof may extend beyond the demarcation 1900. Further, although FIG. 9 shows the IOL 70 as including haptics 450, it is understood that the IOL 70 shown in FIG. 9 may also represent the optic 460 of a two-piece IOL, such as the two-piece IOL 70 shown in FIG. 4, which omits haptics.

The present disclosure describes IOL injectors having a slide advance and a rack and pinion that functions as a linear actuator. The IOL injector 10 described herein is configured to advance an IOL from a storage location to a dwell location by the movement of a plunger. Upon advancing the IOL to the dwell location, a rack and pinion engages and is configured to advance the IOL axially from the dwell location and into the patient's eye.

FIGS. 10A-15D show various exemplary implementations of an IOL injector having the slide advance and rack and pinion. The IOL injectors 10 having the slide advance and rack and pinion includes an injector body 20. The injector body 20 includes a main body 21 having a distal end 22 and a proximal end 50, and an opening 1701 formed in the main body 21, and a first pinion 1702 extending through the opening 1701 and is rotational about a pivot 300. The first pinion 1702 is rotatable within the injector body 21. The injector body 20 also includes a nozzle 25 having a proximal end 23 and a distal end 60. The proximal end 23 of the nozzle 25 is coupled to the distal end 22 of the main body 21. The injector body 20 and nozzle 25 define a bore 40, and a longitudinal axis 75 extends along the bore 40. The nozzle 25 also includes an opening 29 formed at the distal end 60. Although not identified, the IOL injector 10 may also include a storage compartment, similar to the storage compartment 80 described above, and may also include a door, which may be similar to door 90, in order to access the storage compartment, e.g., to install or remove an IOL from a cavity of the storage compartment.

Figure 10A:
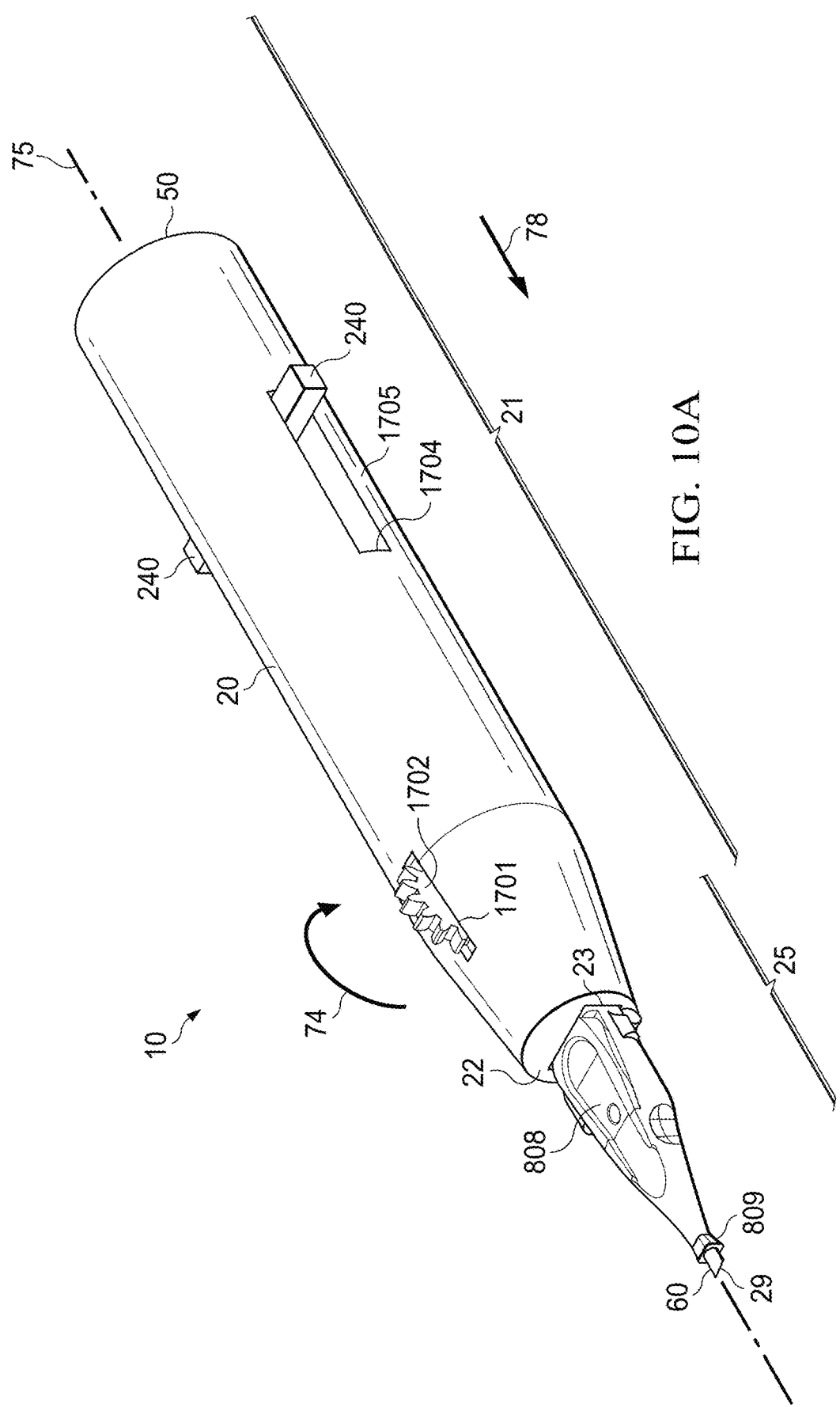
FIG. 10A is a perspective view of an exemplary IOL injector having a slide advance and rack and pinion operable to advance an IOL within the IOL injector.
Figure 10B:
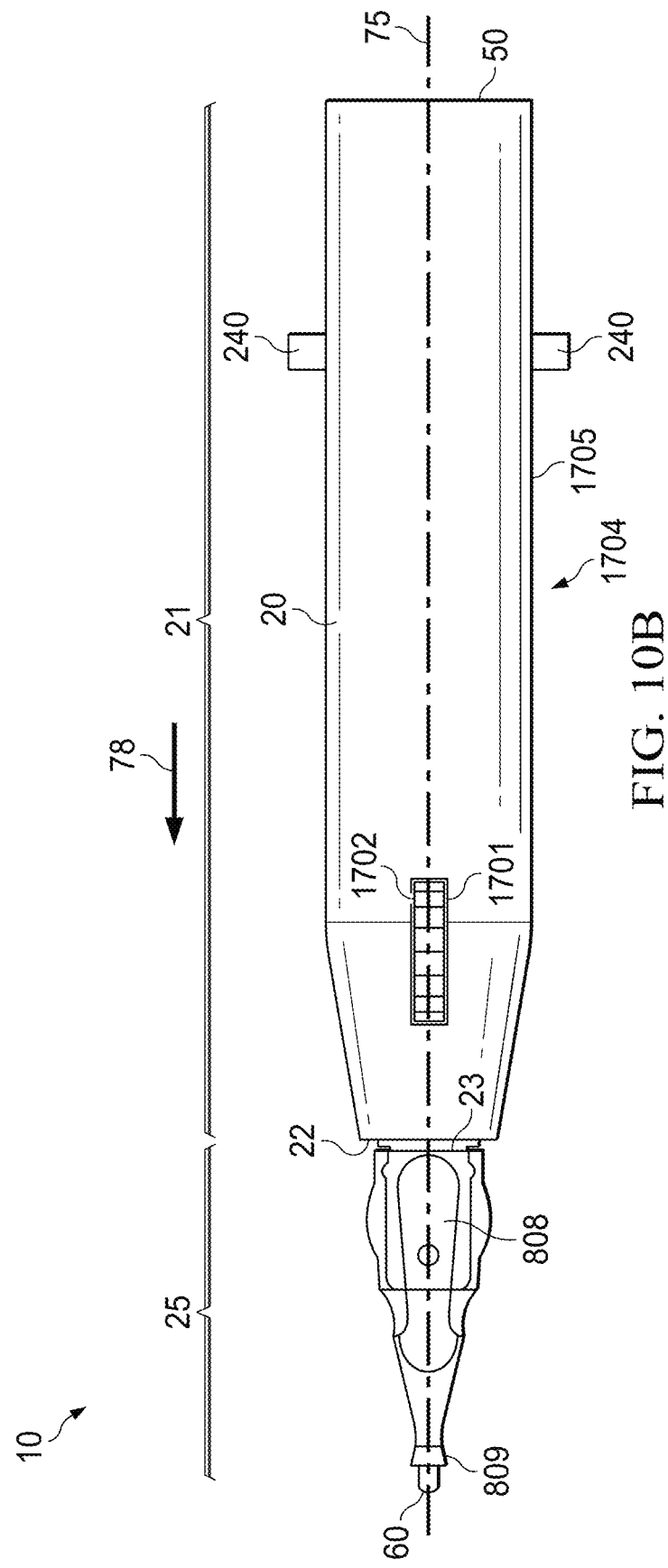
FIG. 10B is a top view of the IOL injector of FIG. 10A.
Figure 10C:
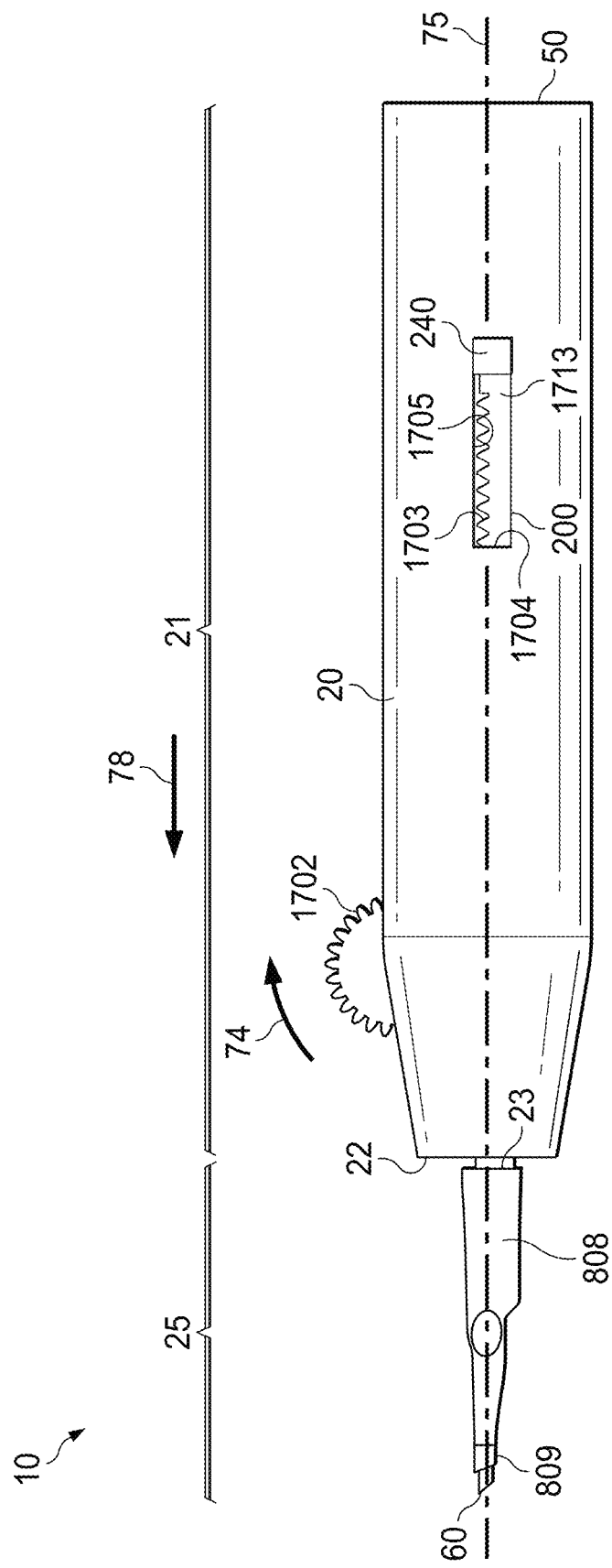
FIG. 10C is a side view of the IOL injector of FIG. 10A.
Figure 10D:
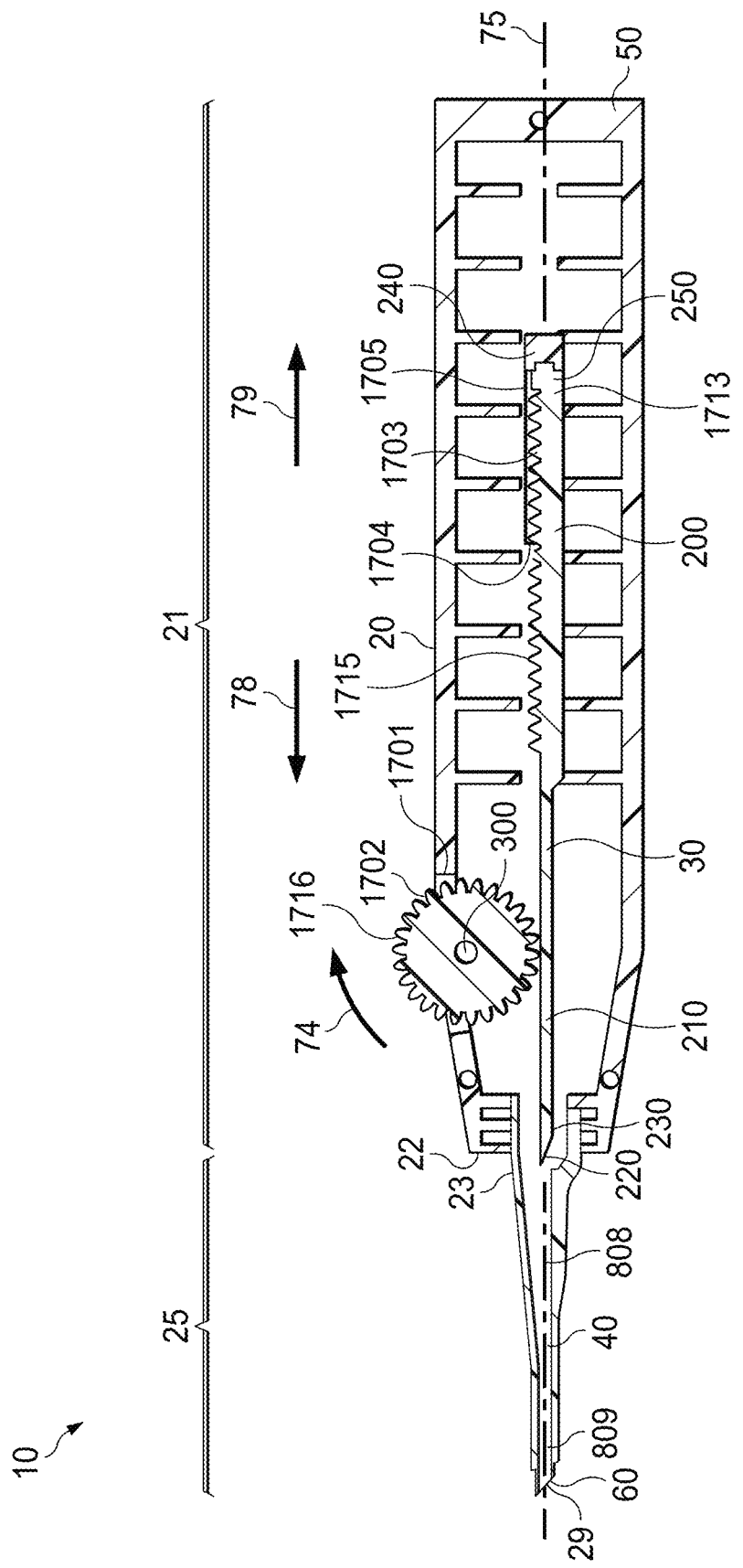
FIGS. 10D and 10E are cross-sectional views of the IOL injector of FIG. 10A.

As shown in FIG. 10D, for example, the IOL injectors 10 also include a plunger 30 disposed inside of the injector body 20 and nozzle 25. The plunger 30 has a proximal end 250 and a distal end 230, is movable within the injector body 20, and is aligned with the bore 40. The plunger 30 includes a plunger body 200, a plunger rod 210, and a plunger tip 220 formed at the distal end 230. A rack 1703 is formed on the plunger body 200 and includes a plurality of teeth 1715. The plunger tip 220 is adapted to engage an IOL disposed at storage location 808 within the nozzle 25 and advance the IOL through the bore 40 formed in the nozzle 25.

In the examples IOL injectors shown in FIGS. 10A-13A, the plunger 30 also includes flanges 240 that extend from the main body 21 via slots 1705. The flanges 240 are disposed at the proximal end 250 of the plunger body 200 and are adapted to be engaged by a user, such as a physician or other medical professional, to slide the plunger 30 in the direction of arrow 78 along the slots 1705. In the illustrated example, the IOL injector includes two slots 1705 formed in the injector body and two flanges 240, one extending through each of the two slots. However, in other implementations, the IOL injector 10 may include a single slot 1705 and a single flange 240 extending therethrough. In still other implementations, the IOL injector 10 may include more than two slots 1705 and two flanges 240.

The first pinion 1702 includes a plurality of teeth 1716 adapted to engage and intermesh with the teeth 1715 of the rack 1703, such that the rack 1703 is movable in a first axial direction indicated by the arrow 78 toward the distal end 60 of the nozzle 25 in response to a rotation of the first pinion 1702 in a first rotational direction indicated by arrow 74. When engaged, the first pinion 1702 and the plunger body 200 cooperate to form a rack and pinion, which is a type of linear actuator that includes a set of gears that convert rotational motion into linear motion. Gear teeth formed on a circular gear, called the "pinion," engages gear teeth formed on a linear gear bar, called the "rack." Rotational force applied to the pinion causes the rack to move relative to the pinion, thereby translating the rotational movement of the pinion into linear movement of the rack.

In a first configuration, as shown, for example, in FIG. 10D, the plunger 30 is in a first, unactuated position where the plunger body 200 is proximal to first pinion 1702. In the first position, the flanges 240 may contact a proximal end 1717. Thus, in the first configuration, the plurality of teeth 1716 of the first pinion 1702 is not engaged with the plurality of teeth 1715 of the rack. The plunger 30 is moveable in response to an axial force applied to the flanges 240 until the flanges 240 contact a barrier 1704. In the illustrated example, the barrier 1704 corresponds to distal ends of the slots 1705. When the flanges 240 engage the barrier 1704 of the slots 1705, the plunger 30 is at a second position, and the IOL injector 10 is in a second configuration. In the second configuration, the plunger body 200 is disposed adjacent to the first pinion 1702 such that the plurality of teeth 1716 of the first pinion 1702 are engaged with the plurality of teeth 1715 of the plunger body 200.

The protrusions 240 may form a continuous body that extends through both slots 1705 and is attached to the proximal end 250 of the plunger body 200. The protrusions may be detachable from the plunger body 200 at detachment location 1713 at the proximal end 250 such that, when the protrusions 240 reach the barrier 1704 of the slots 1705, the protrusions 240 may be detached to permit the plunger 30 to continue distal movement in the direction of arrow 78 as the first pinion 1702 is actuated. For example, in some instances, the protrusions 240 may remain attached to the plunger body 200 until a user begins to actuate the first pinion 1702 to continue to drive the plunger 30 distally in the direction of arrow 78. Thus, the protrusions 240 may be detachable when an axial load in the direction of arrow 78 is applied to the plunger 30 at a location distal to the protrusions 240. Further, one or more of the slots 1705 may include a retaining feature to retain the protrusions 240 at the distal end of the slots 1705. A retaining feature may be useful in preventing the plunger 30 from sliding in the direction of arrow 79 after the plunger 30 has been moved from the first position to the second position due, for example, to a change in orientation of the IOL injector 10. Consequently, the retaining feature would maintain the rack 1703 of the plunger body 200 engaged with the first pinion 1702 regardless of a change in orientation of the IOL injector 10.

Figure 16:
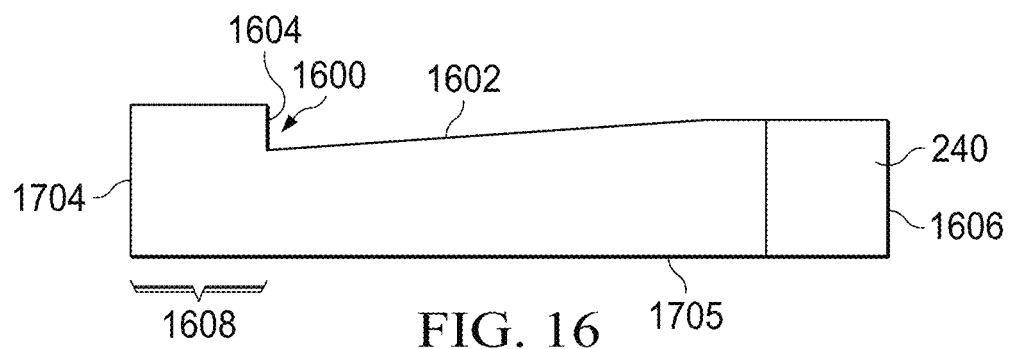
FIG. 16 is a detail view of a slot formed in an injector body of an IOL injector that includes a retaining feature for retaining a plunger in a distal-most position within the slot.

Referring to FIG. 16 shows a detail view of a slot 1705 that includes a retaining feature 1600. In the illustrated example, the retaining feature is a ramp 1602 having a flat end 1604 transverse to a longitudinal axis of the IOL injector, such as axis 75 of the IOL injector 10. Once the plunger 30 is advanced to where the protrusions 240 contact the barrier 1704 of the slot 1705, the flat end 1604 engages a proximal side 1606 of the protrusion 240 to retain the protrusion 240 at a distal position 1608, thereby preventing the protrusion 240 from moving proximally once engaged by the retaining feature 1600.

At the first position, the plunger tip 220 is proximal to the storage location 808 and free from contact with an IOL disposed therein. As the plunger 30 is advanced from the first position to the second position, the distal tip 220 of the plunger engages an IOL disposed at the storage location 808 and advances the IOL distally through the bore 40 (in the direction of arrow 78) until the flanges 240 contact the barrier 1704 of the slots 1705, as which point the IOL is a dwell location 809 within the bore 40 of the nozzle 25. In the second configuration, the first pinion 1702 is operable to continue to advance the plunger 30 in the direction of arrow 78 and delivery the IOL into a patient's eye.

In some implementations, at the second position, the plunger tip 220 will typically be 5 mm to 20 mm proximal to an IOL disposed at the storage location 808 when the plunger 30 is located at the first position, and the plunger tip 200 contacts the IOL, such as the trailing, or proximally oriented, haptic (e.g., haptic 450 of the IOL 70 shown in FIG. 3; a haptic 405 of the base 461 shown in FIG. 4; or a proximal edge 468 of the optic 460 shown in FIG. 4) with the IOL positioned at the dwell location 809, as described above in the context of FIG. 9.

In some implementations, for example as shown in FIGS. 14 and 15A to 15C, the channels 1705 and the flanges 240 may be omitted. In such instances, the plunger 30 extends through an opening formed in the proximal end 50, and a flange 240 is formed at a proximal end 250 of the plunger body 200. An axial force applied to a proximal surface 244 of the flange 240, such as a force applied by a finger of a user, in the direction of arrow 78 is operable to advance the plunger 30 from the first position to the second position.

Figure 15A:
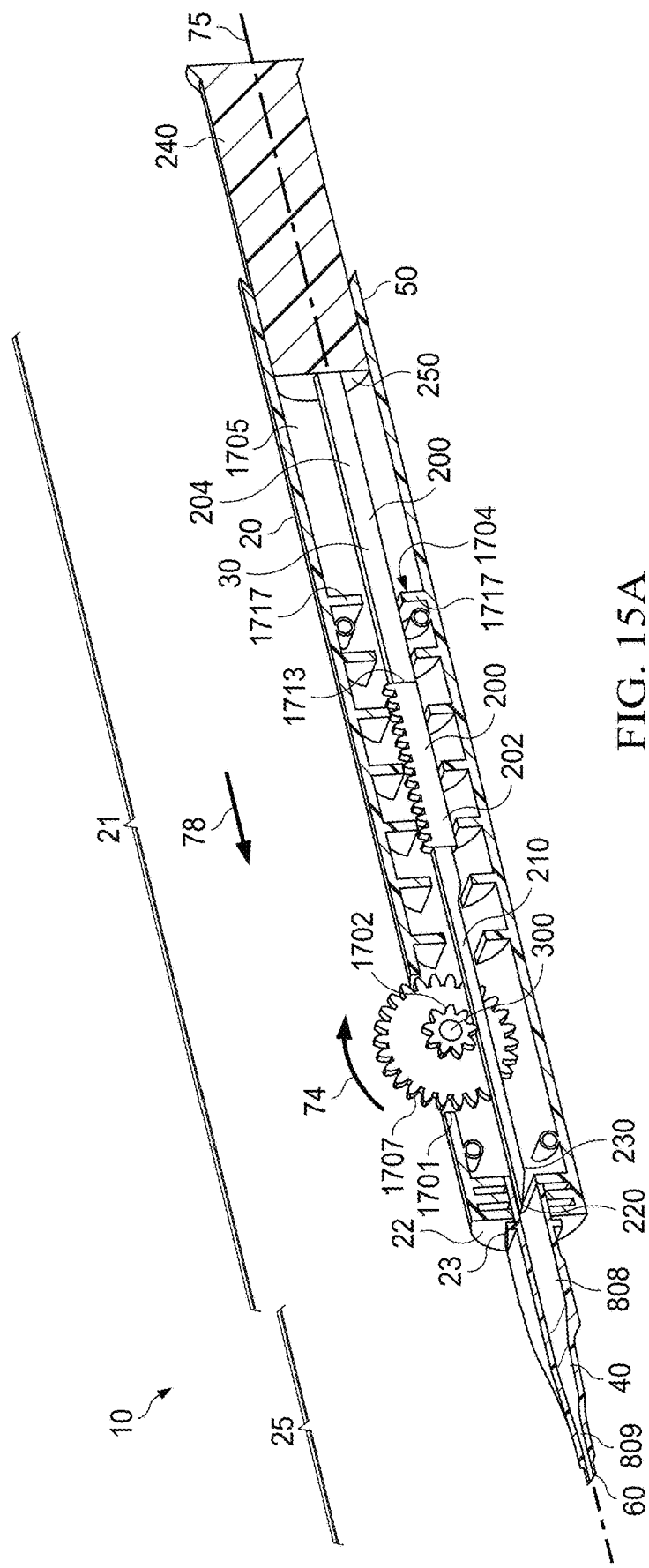
FIGS. 15A-15C are cross-section views of another example IOL injector having a slide advance and a rack and pinion.
Figure 15B:
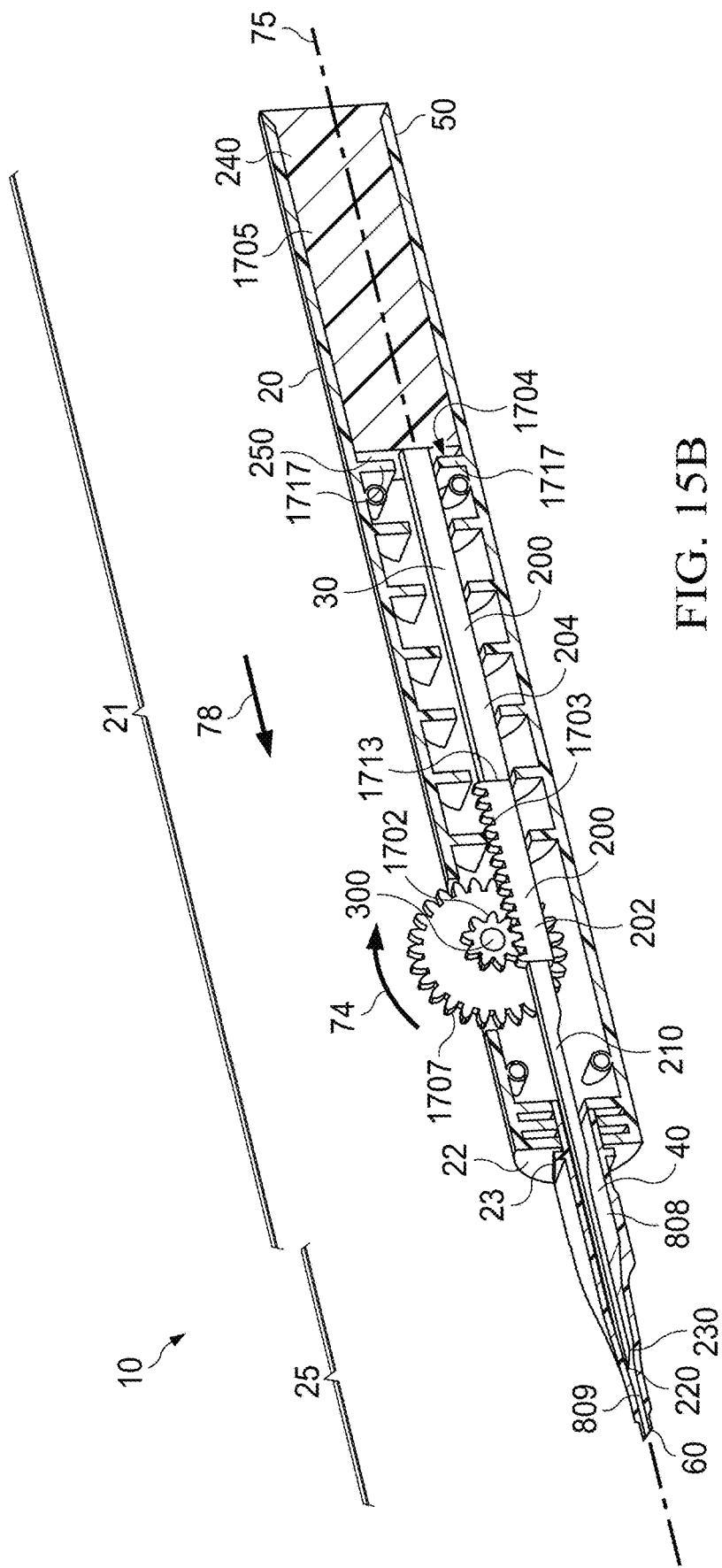
Figure 15C:
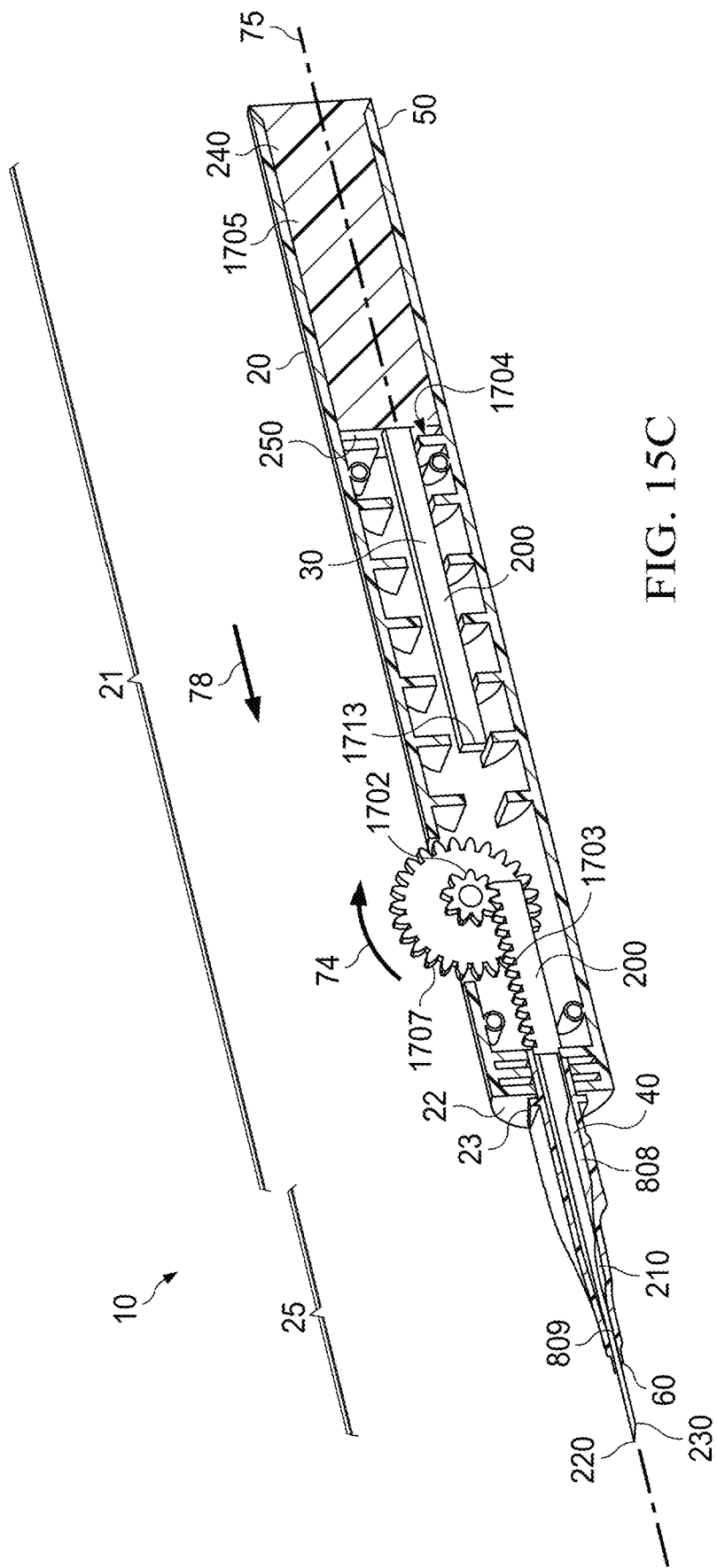

FIGS. 15A to 15C illustrate another example IOL injector 10 in which the plunger body 200 includes a first portion 202 and a second portion 204 that engage each other at a detachment location 1713. In the illustrated example, the first portion 202 of the plunger body 200 includes a rack 1703. However, in other implementations, the rack 1703 may extend along a portion or an entire length of the second portion 204. A flange 240 is formed at a proximal end 250 of the proximal end 250 of the plunger 30. The flange 240 is attached to the second portion 204 of the injector body 200. In other implementations, the first portion 202 and the second portion 204 may be fixedly attached to each other (e.g., integrally formed), and the flange 240 may be separable from the second portion 204 at the proximal end 250 of the plunger where the plunger 30 engages the flange 240.

FIG. 15A shows the IOL injector 10 in a first configuration in which the plunger 30 is at the first, unactuated position. In the first position, the plunger tip 220 is proximally adjacent to the storage location 808. FIG. 15B shows the IOL injector of FIG. 15A with the plunger 30 advanced to the second position in response to application of the axial force to the flange 240 in the direction of arrow 78. In FIG. 15B, the flange 240 is in contact with a barrier 1704, which corresponds to a rib 1717. In the illustrated example, the barrier 1704 is a set of distal most ribs 1717. In other implementations, the barrier 1704 may be a single rib 1717 or other internal feature within the injector body 20 or other part of the IOL injector 10. When the flange 240 contacts the barrier 1704, the plunger 30 is prevented from further advancement in the direction of arrow 78, but the first pinion 1702 is now engaged with the rack 1703 formed on the first portion 202 of the plunger body 200. With the plunger 30 in the second position, as shown in FIG. 15B, the plunger tip 220 is proximally adjacent to the IOL dwell location 809, and an IOL advanced by the plunger tip 220 would now reside in the dwell location 809. Movement of the plunger tip 220 from the second position toward the distal end 60 of the nozzle 25 is actuated by rotation of the first pinion 1702 in the first rotational direction of the arrow 74 when the IOL injector 10. Referring now to FIG. 15C, as a result of rotation of the first pinion 1702 in the first rotational direction of arrow 74, the rack 1703 and, hence, the first portion 402 of the plunger body 200, advances in the direction of arrow 78 causing the first portion 202 and the second portion 204 of the plunger body 200 to separate. As a result, the position of the second portion 404 and flange 240 upon rotation of the first pinion 1702 in the first rotational direction of arrow 74 remains unchanged.

Figure 14:
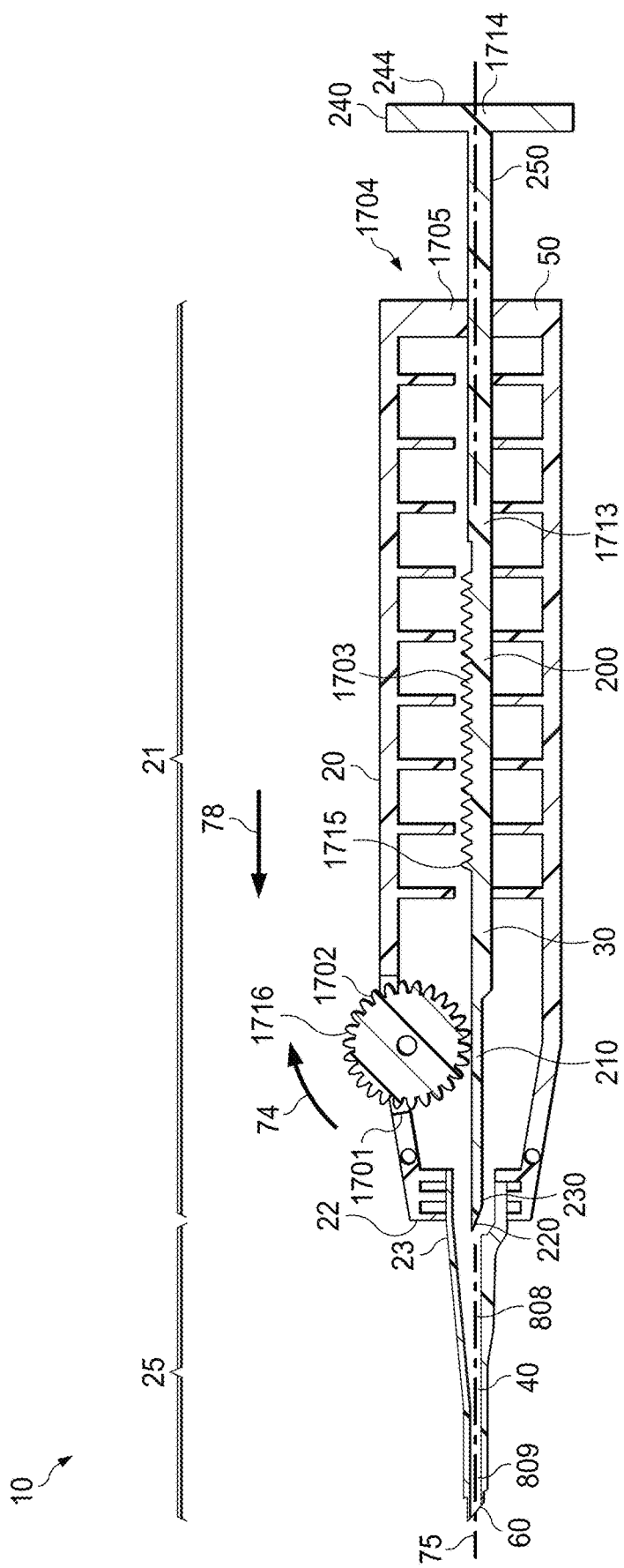
FIG. 14 is a cross-section view of another example IOL injector having a slide advance and rack and pinion.

Other configurations of the IOL injector 10 to allow decoupled movement of the first portion 202 and the second portion 204 of the plunger 30 are also possible. For example, in some implementations, instead of detachment of the first portion 202 of the plunger 30 from the second portion 204 of the plunger 30 at the detachment location 1713 as shown in FIG. 15A-C, the flange 240 may be foldable. For example, the flange 240 may have a hinge at a location where the flange 240 is coupled to the plunger body 200. A hinge may, for example, be located at position 1714 as shown in FIG. 14, such that the flange 240 is adapted to fold and be received into the bore 40 of the main body 21 as the first pinion 1702 is rotated. In other implementations, movement of the plunger 30 from the first position to the second position may be accomplished with the use of a separate, decoupled pushing tool. The pushing tool may be used in place of the flange 240.

In some implementations, the IOL injector may have slots, which may be similar to slots 1705. The slots may extend farther towards the distal end 22 of the main body 21 of the injector body 20 than those shown, for example, in FIGS. 10A and 10C. In those implementations, the barrier 1704 may be a removable barrier insertable into the slots 1705. The removable barrier 1704 may be removed prior to advancement of the plunger tip 220 from the second position toward the distal end 60 of the nozzle 25, such as to deliver an IOL into a patient's eye. Once the removable barrier is removed, the protrusions 242 may are permitted to continue to move distally with the plunger 30 as the second pinion 1702 is rotated to cause the plunger 30 to advance in the direction of arrow 78.

Figure 10E:
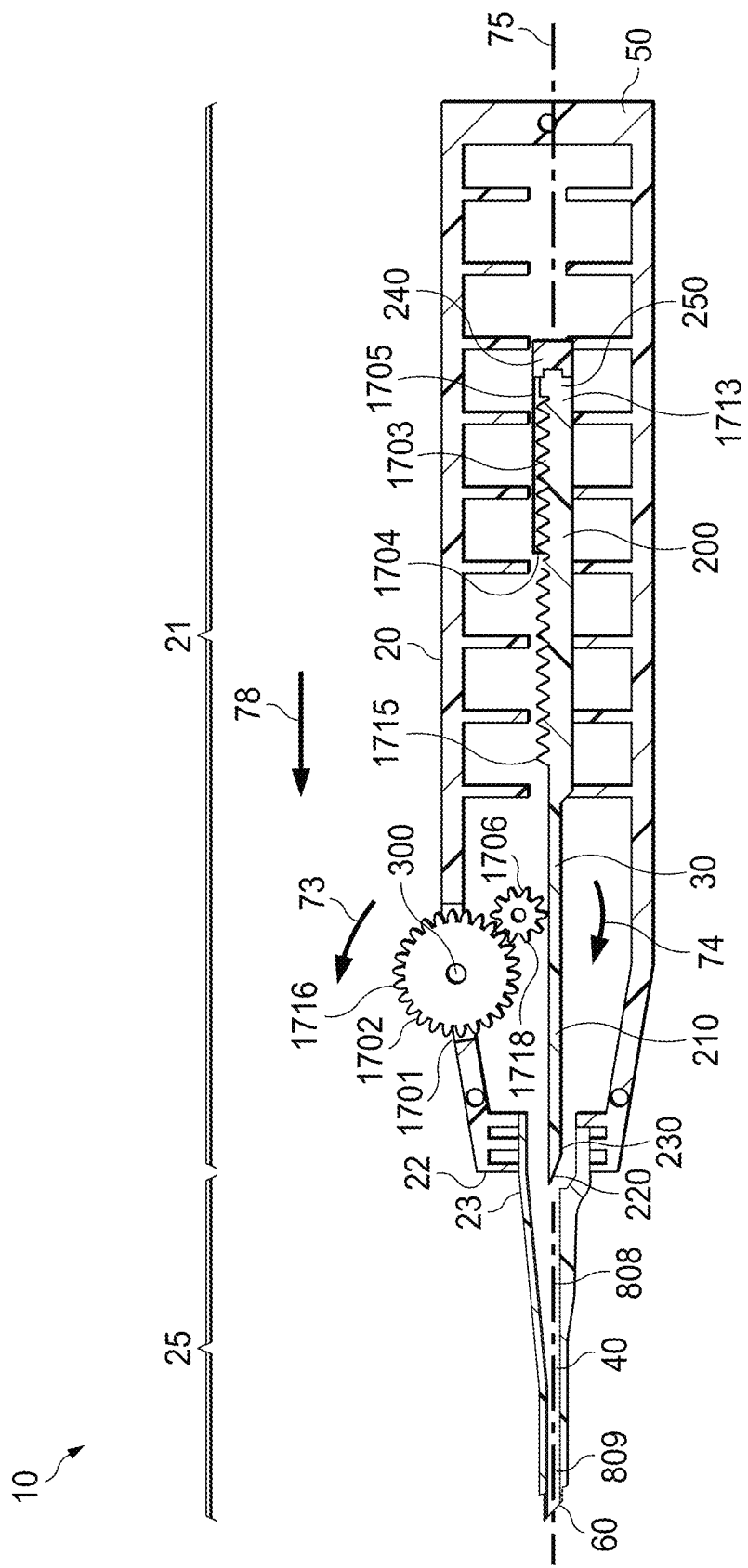

Other implementations may have other rack and pinion arrangements. FIG. 10E, for example, shows an IOL injector 10 that may be similar to the IOL injector shown in FIG. 10D except that the IOL injector 10 of FIG. 10E includes a second pinion 1706 interposed between the first pinion 1712 and the rack 1703. The second pinion 1706 includes a plurality of teeth 1718 adapted to intermesh with the plurality of teeth 1715 of the rack 1703 and the plurality of teeth 1716 of the first pinion 1702. The second pinion 1706 rotates in response to the rotation of the first pinion 1702, and the rack 1703 moves axially in response to the rotation of the second pinion 1706. Accordingly, in response to the rotation of the first pinion 1702 in a second rotational direction of arrow 73, the second pinion 1706 is adapted to rotate in the first rotational direction of arrow 74 and the rack 1703 is adapted to move in the direction of arrow 78 towards the distal end 60 of the nozzle 25. Thus, in the context of the example IOL injector 10 shown in FIG. 10D, axial movement of the plunger 30 in the direction of arrow 78 may be actuated by rotating the first pinion 1702 in the direction of arrow 74, whereas, in the context of the example IOL injector 10 shown in FIG. 10E, rotation of the first pinion 1702 in the second rotational direction of arrow 73. It is further within the scope of the present disclosure to have a rack and pinion arrangement with more than two pinions or rotary gears.

In some implementations, the rack and pinion may provide a mechanical advantage. For example, in some instances, the first pinion 1702 and the second pinion 1706 have different diameters corresponding to different circumferences and, accordingly, different numbers of teeth on each pinion. For example, a ratio of the circumference of the first pinion 1702 to the circumference of the second pinion 1706 may be from 1:1 to 5:1. In some instances, the ratio may be, or be about, 2:1 or 3:1. A ratio greater than 1:1 provides a mechanical advantage that decreases a force the user has to apply to advance an IOL from the dwell location and out of the IOL injector.

A length of the plunger 30 and/or a length of movement of the plunger 30 from the first position to the second position may be selected such that an IOL within the storage location 808 engaged by the plunger tip 220 as the plunger 30 moves from the first position to the second position results in the IOL be positioned within the dwell location, as described herein. Additionally, with the plunger 30 at the second position and the IOL at the dwell location 809, the rack 1703 may be engaged with a pinion (e.g., either the first pinion 1702 for a rack and pinion that includes a single pinion or rotary gear, or the second pinion 1706 in a rack and pinion that includes two pinions or rotary gears). As also explained, the second position of the plunger 30 may correspond to a portion of the plunger 30 engaged with a barrier, such as the barriers 1740 described herein.

FIGS. 10A-10E and 14 show IOL injectors 10 in which the first pinion 1702 is accessible to a user. Accordingly, the user is able to rotate the first pinion 1702 by directly contacting the first pinion 1702. Further, the plurality of teeth 1716 provides a textured surface that provides tactile feedback to a user. Such a textured surface may provide better control of rotation of the first pinion 1702 and, hence, a more controlled delivery out of the IOL injector.

Figure 11:
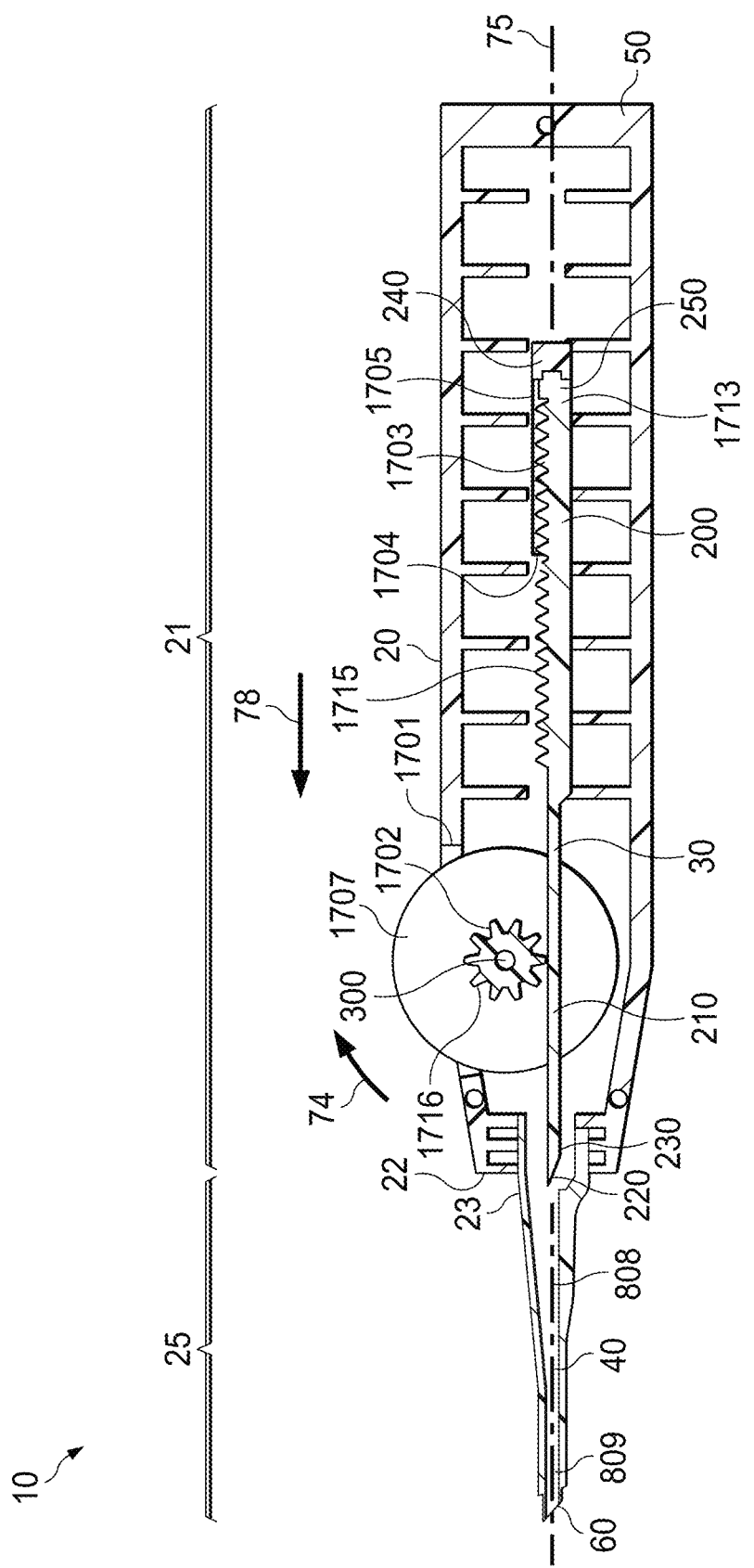
FIG. 11 is a cross-sectional view of a further example IOL injector having a slide advance and rack and pinion.

In other implementations, the IOL injector 10 may include a wheel 1707 coupled to the first pinion 1702 and accessible to a user through the opening 1701 (as shown in FIGS. 11 and 15A-15C) and rotatable about pivot 300. The first pinion 1702 is rotatable with and in a same rotational direction as the wheel 1707. For example, in some implementations, the first pinion 1702 may be fixedly coupled to the wheel 1707, and the wheel 1707 may be rotatably coupled to the main body 21 about pivot 300. Accordingly, in some implementations, the first pinion 1702 may or may not extend through the opening 1701 and outside the injector body 20, but the wheel 1707 extends through the opening 1701 and outside the injector body 20 such that the user is able to rotate the wheel 1707. As the wheel 1707 rotates, the first pinion 1702 rotates with the wheel 1707. In some implementations, a ratio of the diameter of the wheel 1707 to the diameter of the first pinion 1702 may be from 1:1 to 5:1. In particular, the ratio may be, or be about, 2:1 or 3:1. In some instances, the wheel 1707 may have a geared or otherwise textured surface (as shown, for example, in FIGS. 15A-15C) or a smooth, untextured surface (as shown, for example, in FIG. 11). Thus, in some implementations, the rack and pinion may be operated by a user rotating the first pinion 1702 directly or the wheel 1707 directly, e.g. using a finger or thumb. In some implementations, the wheel 1707 may have a circular shape as shown in FIG. 11. In other implementations, the wheel 1707 may have another shape, such as an oblong, oval, faceted, or other type of shape. Further, the wheel 1707 may have one or more surface features that provide a convenient placement for a user's finger or thumb at one or more positions along the surface of the wheel 1707. In addition, the ratio of a size of the wheel 1707 (e.g., diameter) to a size of the first pinion 1702 (e.g., diameter) may provide a mechanical advantage.

Figure 12:
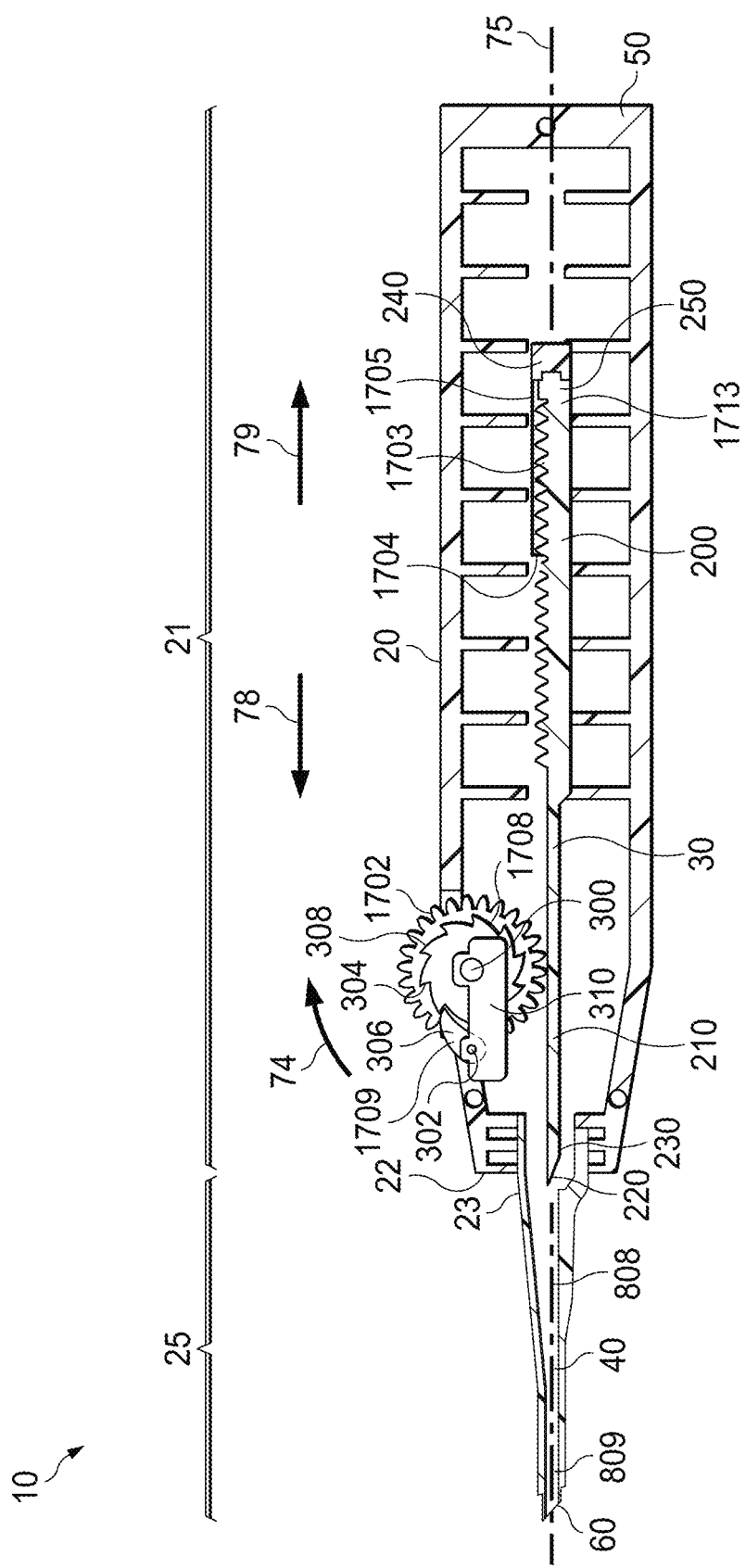
FIG. 12 is a cross-sectional view of another exemplary IOL injector having a slide advance and ratcheted rack and pinion.

FIG. 12 shows an example IOL injector 10 that includes a ratchet that permits rotation of the first pinion 1702 in a first direction but prevents rotation of the first pinion 1702 in a second direction opposite the first direction. The ratchet includes a wheel 1708 and a pawl 1709 that interact to prevent movement of the plunger 30 in the direction of arrow 79 away from the distal end 60 of the nozzle 25. The wheel 1708 is coupled to the first pinion 1702 at a pivot 300. The wheel 1708 and the first pinion 1702 rotate together. The pawl 1709 is coupled to the main body 21 at a pivot 302. In other implementations, the pawl 1709 may be coupled to the first pinion 1702 and the wheel 1708 may be coupled to the main body 21. As shown in FIG. 12, the pawl 1709 and wheel 1708 interact such that the first pinion 1702 is permitted to rotate in a single direction, i.e., in the rotational direction of arrow 74. The pivots 300 and 302 may be retained on an elongated beam 310.

In the example shown, the wheel 1708 has a saw blade shape that includes a plurality of radial surfaces 304, and the pawl 1709 includes a freely extending end 306. The first pinion 1702 and wheel 1708 are free to rotate together in the rotational direction of arrow 74. As the first pinion 1702 and ratchet 170 rotate in the rotational direction of arrow 74, the pawl 1709 follows an exterior surface 308 of the wheel 1708 and does not interfere with rotation of the first pinion 1702. If an attempt were made to reverse the rotational direction of the first pinion 1702, the freely extending end 306 of the pawl 1709 would engage with one of the radial surfaces 304 of wheel 1708 and prevent rotation of the first pinion 1702.

Figure 13A:
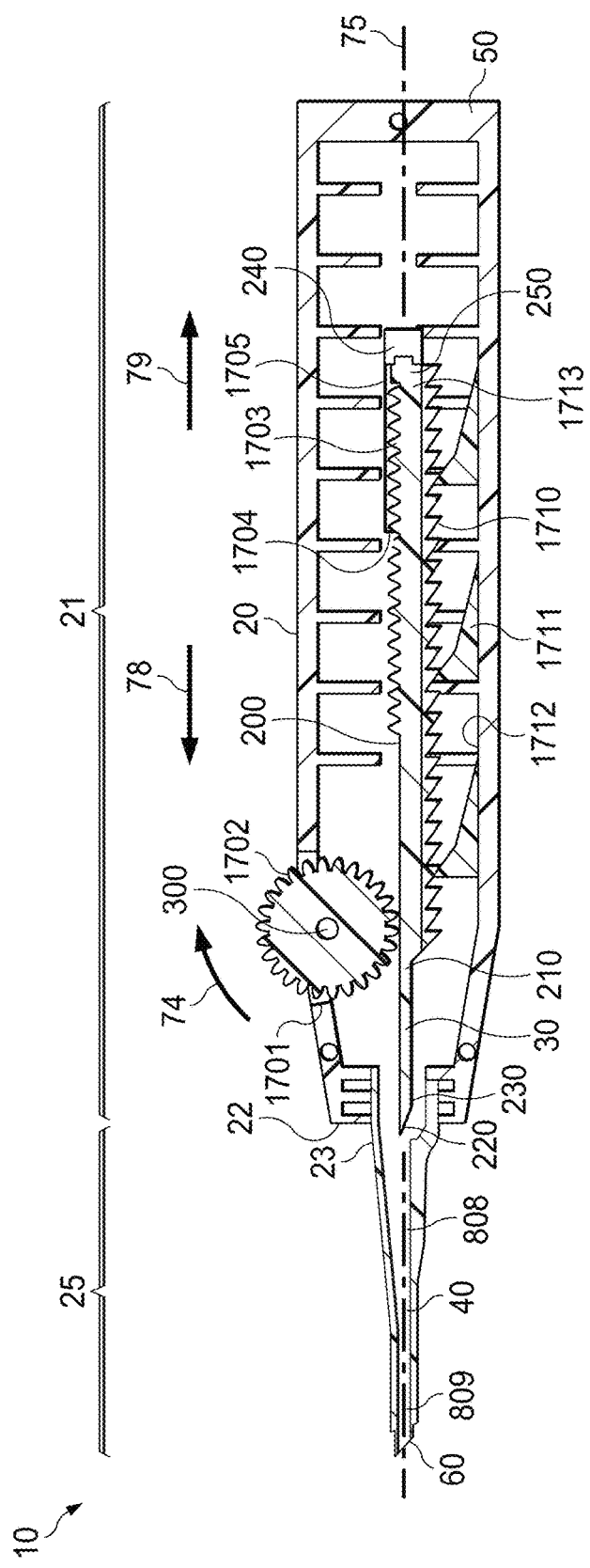
FIG. 13A is a cross-sectional view of further example IOL injector having a slide advance and rack and pinion.

FIG. 13A shows another example IOL injector 10 that includes a ribbed damper that is configured to provide a frictional resistance to the axial movement of the plunger 30. The ribbed damper includes at least one rib 1710 on the plunger body 200 and at least one rib 1711 on an interior wall 1712 of the main body 21. The ribs 1710 are in the form of a ramp that increases in height in the distal direction. The ribs 1711 are in the form of a ramp that increases in size height towards the proximal direction. The at least one rib 1710 on the plunger body 200 is configured to contact the at least one rib 1711 on the interior wall 1712 and generate a frictional force that resists axial movement of the plunger 30 in the direction of arrow 78, while not preventing movement of the plunger 30 in the direction of arrow 78. The ribbed damper may be composed of flexible material, such as deformable plastic.

Figure 13B:
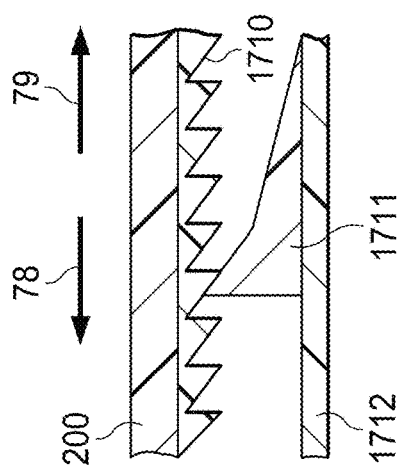
FIG. 13B a detail view of a portion of the IOL injector of FIG. 13A.

FIG. 13B is a detail view of an exemplary ribbed damper. As shown in FIG. 13B, one or more of the ribs 1710 on the plunger body 200 of the plunger 30 may form a ridge and one or more ribs 1711 on the interior wall 1712 may form a ridge-engaging tooth, wherein the ridge and the ridge-engaging tooth are adapted to prevent movement of the plunger 30 in a second axial direction, i.e., in the direction of arrow 79. Thus, the one or more ribs 1710 on the plunger body 200 of the plunger 30 and the one or more ribs 1711 on the interior wall 1712 may form a ratchet that permits movement of the plunger 30 in the direction of arrow 78 but prevents movement of the plunger 30 in the direction of arrow 79.

In some implementations, the one or more ribs 1710 and/or 1711 may be a plurality of ribs 1710 and/or 1711, and a distance between each of the ribs 1710 and/or 1711 may decrease with decreasing distance from the distal end 22 of the main body 21. Accordingly, having a closer placement of the ribs 1710 and/or 1711 toward the distal end 22 of the plunger body 200 and/or interior wall 1712 of the bore 40 may provide increased resistance to counteract the typically high peak axial force experienced when the IOL 70 passes through the exit of the opening 29.

In some implementations, the first pinion 1702 or the wheel 1707 may be closer to the distal end 22 of the main body 21 than the proximal end 50 of the main body 21. For example, in some implementations, the first pinion 1702 or the wheel 1707 may be located from 1 cm to 7 cm from the distal end 22 of the main body 21.

Figure 17:
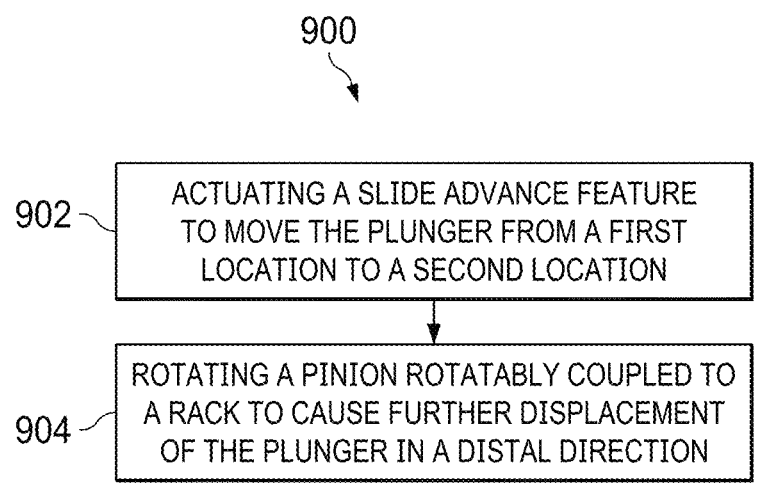
FIG. 17 is an example method of operation of an IOL injector.

The present disclosure also relates to methods of injecting an IOL into an eye. In the case of IOL injectors described herein that have a slide advance feature and rack and pinion, an example method 900 is shown in FIG. 17. The method 1700 includes a step 902 of actuating the slide advance feature by applying an axial force to the plunger, thereby moving the plunger tip from a first position proximally adjacent to the IOL storage location to a second position proximally adjacent to the IOL dwell location. In the course of moving the plunger from the first position to the second position, an IOL stored in the storage location may be placed in the dwell location when the plunger is located as the second position. In some implementations, the axial force may be applied to flange, which may be similar to flange 240. The method also includes a step 904 in which a pinion rotatably coupled with a rack is rotated to cause further displacement of the plunger in the distal direction. The further distal displacement of the plunger may be used to eject an IOL from a distal opening of the IOL injector.

Various implementations of the IOL injector described herein and within the scope of the present disclosure may be configured to deliver an IOL base and/or an IOL optic of a multi-piece IOL or a one-piece IOL. Various implementations of the IOL injectors and associated methods described herein may be used with an IOL base and/or the optic that are manually loaded into the IOL injector by a user or pre-loaded therein prior to delivery of the IOL injector to a user.

Non-limiting examples of IOL injectors that may be adapted for use with the IOL compressor as described herein include those described in U.S. Pat. No. 7,156,854 and U.S. Patent Application Publication No. 2016/0256316, the disclosures of each being incorporated herein by reference in their entireties.

Advantages of the IOL injectors described herein include but are not limited to the following. In various implementations, IOL injectors described herein having the slide advance and rack and pinion allows a user to advance an IOL out of the IOL injector using one hand. The slide advance is operable to advance the IOL a selected axial travel distance from a storage location to a dwell location and obviates a need for the user to make a judgement (e.g. by visual inspection of the IOL within the nozzle) as to whether the IOL has been advanced to the dwell location. The slide advance, thus, reduces variation and provides for a more consistent operation and performance of the IOL injector. Additionally, having two different features for advancing the IOL within the IOL injector in sequence, i.e., one for advancing the IOL from the storage location to the dwell location and other for advancing the IOL from the dwell location to ejection from the IOL injector, reduces the possibility that the user will perform the tasks out of order. In order to engage the components of the rack and pinion, the plunger is advanced to the first position, where the plunger tip is proximally adjacent to the dwell location. In some implementations, a ratio applicable to the rack and pinion may be selected to reduce a force supplied by the user to accomplish advance the IOL via the rack and pinion. In addition, IOL injectors described herein may have a first pinion (or wheel) located proximate to a distal portion of an injector body, which may provide a user with increased control.

The above-disclosed subject matter is to be considered illustrative, and not restrictive, and the appended claims are intended to cover all such modifications, enhancements, and other implementations that fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

The invention claimed is:

1. An intraocular lens (IOL) injector comprising:
  an injector body comprising:
    a main body;
    a nozzle coupled to a distal end of the main body;
  a bore extending through the nozzle; and
  a pinion pivotably coupled to the injector body and comprising a plurality of teeth; and
  a plunger at least partially disposed in the injector body and moveable therein, the plunger comprising:
    a plunger body
    a rack disposed on the plunger body and comprising a plurality of teeth, the pinion and the rack interoperable to advance the plunger in a first axial direction towards a distal end of the nozzle in response to a rotation of the pinion;
    a plunger rod coupled to a distal end of the plunger body;
    a plunger tip formed at a distal end of the plunger rod, the plunger tip adapted to contact an IOL; and
    a flange disposed at a proximal end of the plunger body, wherein the main body comprises a barrier formed therein and a proximal opening, and wherein the flange is moveable into the proximal opening of the main body and engageable with the barrier to define a second position when the plunger is distally displaced within the injector body,
  the plunger movable a first distance within the injector body in response to an axial force applied to the plunger free from engagement between the rack and the pinion, and, the plunger moveable in response to rotation of the pinion over a second distance within the injector body when the pinion is rotatably coupled with the rack and the plunger.

2. The IOL injector of claim 1, wherein the main body further comprises a slot, wherein the plunger further comprises a flange extending through the slot, and wherein the flange is displaceable in the slot to move the plunger from a first position to the second position.

3. The IOL injector of claim 2, wherein movement of the flange from the first position to the second position is operable to displace an IOL from a storage position in the nozzle to a dwell position in the nozzle.

4. The IOL injector of claim 2, wherein movement of the plunger from the first position to the second position moves the plurality of teeth of the pinion and the plurality of teeth of the rack from an unmeshed relationship into an intermeshing relationship.

5. The IOL injector of claim 2, further comprising a barrier adapted to engage the flange to define the second position.

6. The IOL injector of claim 1, wherein the flange is detachable from the plunger.

7. The IOL injector of claim 1 wherein the first plurality of teeth of the pinion are adapted to intermesh with the plurality of teeth of the rack such that rotation of the pinion in a first rotational direction displaces the plunger in the first axial direction.

8. The IOL injector of claim 1, wherein the pinion is a first pinion, wherein the IOL injector further comprising a second pinion interposed between the first pinion and the rack, and wherein the rotation of the first pinion in a first rotational direction displaces the plunger in the first axial direction.

9. The IOL injector of claim 8, wherein the second pinion comprises a plurality of teeth that intermeshes with both the plurality of teeth of the first pinion and the plurality of teeth of the rack.

10. The IOL injector of claim 9, wherein a ratio of a diameter of the first pinion to a diameter of the second pinion is in a range of 1:1 to 5:1.

11. The IOL injector of claim 10, wherein the ratio is 3:1.

12. The IOL injector of claim 1, further comprising a wheel coupled to the pinion and accessible to a user, wherein the pinion is rotatable in response to a rotation of the wheel.

13. The IOL injector of claim 1, further comprising a ratchet and pawl adapted to permit rotation of the pinion in a first rotational direction and prevent rotation of the pinon in a second rotational direction opposite the first rotational direction.

14. The IOL injector of claim 1, wherein the IOL injector further comprises a ribbed damper comprising at least one rib on the plunger body and at least one rib on an interior wall of the main body, wherein the at least one rib on the plunger is adapted to contact the at least one rib on the interior wall and to provide frictional resistance to movement of the plunger in the first axial direction.

15. The IOL injector of claim 14, wherein one or more of the ribs on the plunger body forms a ridge and the at least one rib on the interior wall forms a ridge-engaging tooth, wherein the ridge and the ridge-engaging tooth are adapted to prevent movement of the plunger in a second axial direction opposite the first axial direction.

16. The IOL injector of claim 14, wherein one or more of the ribs on the interior wall forms a ridge and the at least one rib on the plunger forms a ridge-engaging tooth, wherein the ridge and the ridge-engaging tooth are adapted to prevent movement of the plunger toward the proximal opening of the main body of the IOL injector.

17. The IOL injector of claim 1, wherein the IOL injector is adapted to separately inject an IOL base, an IOL optic, or both.

18. The IOL injector of claim 1, wherein the IOL injector is adapted to concurrently inject an IOL base and an IOL optic.

* * * * *